(12) United States Patent
Shibata et al.

(10) Patent No.: US 7,400,393 B2
(45) Date of Patent: Jul. 15, 2008

(54) METHOD AND APPARATUS FOR DETECTING DEFECTS IN A SPECIMEN UTILIZING INFORMATION CONCERNING THE SPECIMEN

(75) Inventors: Yukihiro Shibata, Fujisawa (JP); Shunji Maeda, Yokohama (JP); Hidetoshi Nishiyama, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/478,617

(22) Filed: Jul. 3, 2006

(65) Prior Publication Data

US 2007/0058164 A1    Mar. 15, 2007

(30) Foreign Application Priority Data

Sep. 9, 2005    (JP)    ............................. 2005-261564

(51) Int. Cl.
     *G01N 21/88*    (2006.01)
(52) U.S. Cl. ............... 356/237.5; 356/237.2; 356/237.4; 356/237.1; 356/401
(58) Field of Classification Search .............. 356/237.1, 356/237.2–237.5
See application file for complete search history.

(56) References Cited

U.S. PATENT DOCUMENTS

| | | | | |
|---|---|---|---|---|
| 5,963,314 | A * | 10/1999 | Worster et al. ........... | 356/237.2 |
| 6,693,293 | B2 * | 2/2004 | Oomori et al. ........... | 250/559.4 |
| 2001/0048522 | A1 * | 12/2001 | Yonezawa ................ | 356/237.2 |
| 2002/0093647 | A1 * | 7/2002 | Fukazawa et al. ......... | 356/237.1 |
| 2004/0075837 | A1 * | 4/2004 | Maeda et al. ............. | 356/394 |
| 2004/0109157 | A1 * | 6/2004 | Kim et al. ................ | 356/237.1 |
| 2005/0213086 | A1 * | 9/2005 | Hamamatsu et al. ...... | 356/237.2 |
| 2005/0231713 | A1 * | 10/2005 | Owen et al. .............. | 356/237.1 |
| 2006/0197946 | A1 * | 9/2006 | Biellak et al. ............ | 356/237.4 |

FOREIGN PATENT DOCUMENTS

| | | |
|---|---|---|
| JP | 2004-055695 | 2/2004 |
| JP | 2004-087820 | 3/2004 |

* cited by examiner

*Primary Examiner*—Layla G. Lauchman
*Assistant Examiner*—Rebecca C Slomski
(74) *Attorney, Agent, or Firm*—Antonelli, Terry, Stout & Kraus, LLP.

(57) ABSTRACT

This invention provides a defect inspection method and apparatus that can easily and quickly determine, from among a plurality of inspection conditions, a condition that allows for an inspection with high sensitivity. The inspection apparatus has a variety of optical functions to cover a variety of kinds of defects to be inspected (shape, material, nearby pattern, etc.). For each optical function, grayscale depths of defects that the operator wants detected and of pseudo defects that he or she wants undetected are accumulated for future use, so that conditions conducive to a higher sensitivity and a lower pseudo defect detection rate can be selected efficiently. Conditions that can be selected for optical systems include a bright-field illumination, a dark-field illumination and a bright-/dark-field composite illumination, illumination wavelength bands, polarization filters and spatial filters.

7 Claims, 13 Drawing Sheets

METHOD AND APPARATUS FOR DETECTING DEFECTS IN A SPECIMEN UTILIZING INFORMATION CONCERNING THE SPECIMEN

The present application claims priority from Japanese application JP2005-261564 filed on Sep. 9, 2005, the content of which is hereby incorporated by reference into this application.

BACKGROUND OF THE INVENTION

The present invention relates to a method for inspecting microfine patterns for defects and foreign substances, the microfine patterns being formed on a substrate in a thin-film process represented by a semiconductor manufacturing process and a flat panel display manufacturing process. The invention also relates to an apparatus using such an inspection method.

As a conventional semiconductor inspection apparatus, JP-A-2004-55695 discloses a construction that uses a laser beam to check for defects in semiconductor photo masks and wafers. The light source is a laser and thus an illumination wavelength is a single wavelength.

JP-A-2004-87820 discloses a method and system to search and reference past data on inspection conditions of similar products and set new inspection conditions.

For example, a semiconductor wafer to be inspected has wiring patterns arranged in multiple layers, with an interlayer insulating film formed between the pattern layers for electric insulation. There are two types of the optical semiconductor wafer inspection apparatus, a bright field illumination type and a dark field illumination type. Both of these types perform inspections mainly by comparing images of dies on which patterns of the same design are formed. To enhance the inspection sensitivity of the image comparison system, it is desired that pseudo defects the apparatus user defines not be seen on the image. The pseudo defects include brightness differences between detected images corresponding to thickness differences between interlayer insulating films, and also grains. Generally, since the pseudo defects do not have adverse effects on electric characteristics of semiconductor devices, the apparatus user wants these pseudo defects left undetected. For this reason, it is unavoidable to raise a defect decision threshold for a difference image calculated from the image comparison so as to allow the pseudo defects.

The brightness differences between detected images that depend on the thickness differences between interlayer insulating films and which constitute the pseudo defects, become large as the illumination wavelength width narrows and small as it widens. That is, the effects that the thickness variations of the interlayer insulation films have on the brightness variations of the detected images increases as the wavelength width of the illumination light decreases. Therefore, to reduce the brightness differences between detected images caused by the thickness differences between interlayer insulating films, it is advantageous to widen the wavelength width of the illumination light. This makes it possible to reduce the defect decision threshold. As a result, the possibility of being able to detect fine defects of small grayscale depths becomes high, contributing to an enhanced level of detection sensitivity. Thus, in the image comparison-based inspection, when an illumination light of single wavelength, such as disclosed in JP-A-2004-55695, is used, the grayscale variations of the pseudo defects may increase degrading the inspection sensitivity. Further, on the wafer to be inspected there are various kinds of defects as well as pseudo defects that are preferably not detected.

Since grayscale variations of these defects and pseudo defects change with the illumination wavelength, it is advantageous in terms of enhancing the defect detection sensitivity to select a wavelength range for an illumination light that increases a contrast of defects and reduce brightness variations (grayscale depths) of pseudo defects. With the invention disclosed in JP-A-2004-55695, since a laser is used, the wavelength is a single wavelength and there is no room for wavelength selection. Therefore, when detecting defects by using a particular wavelength, as disclosed in JP-A-2004-55695, some kind of defects may get a large grayscale depth and some kind may fail to get a sufficient grayscale depth. So, to increase a detection rate for a wide range of defects, it is useful if a function to choose an appropriate wavelength for inspection is available.

To realize a higher inspection sensitivity, optical means to increase the grayscale depth of defects are necessary.

When a plurality of optical means are used to further increase the grayscale depth of defects, there are problems that finding optimum conditions takes time and that determining the optimum conditions is difficult.

Further, JP-A-2004-87820 discloses a method that sets new inspection conditions by searching past data on inspection conditions of similar products. This method, however, does not consider changing the illumination wavelength range as one of the inspection conditions according to the material of the wiring pattern of a specimen. In other words, it does not consider setting an inspection condition that best matches defects of various kinds and pseudo defects that preferably are left undetected, both present on the wafer.

SUMMARY OF THE INVENTION

To solve the problems experienced with the conventional technologies, the present invention provides a defect inspection method that uses an illumination system capable of illuminating a specimen with light from a light source having a wide range of wavelength of emitted light, and which retrieves and references past optical inspection conditions used for the same wiring material as the specimen being inspected and selects an appropriate illumination wavelength band that produces a large grayscale depth for defects.

According to one aspect, this invention provides a defect inspection apparatus comprising: a light source means for emitting beams of a plurality of wavelength bands; a light radiation means for selecting a beam of a desired wavelength from among the beams of the plurality of wavelength bands emitted by the light source means and radiating the selected beam onto a specimen formed with a wire pattern; a detection means for receiving an optical image of the specimen, radiated with the beam of the desired wavelength from the light radiation means and formed with the wire pattern, and for outputting an image signal; an image processing means for processing the image signal output from the detection means to detect defects; a control means for controlling at least one of the light source means, the light radiation means, the image detection means and the image processing means; an inspection information database means having a database associated with the specimen and a database associated with optical conditions of at least one of the light source means, the light radiation means, the image detection means and the image processing means; and an input means for inputting information associated with the specimen; wherein the light radiation means has a wavelength selection unit and a plurality of optical systems; wherein the control means, based on information associated with a material of the wire pattern of the specimen input from the input means, controls the wavelength selection unit to select a beam of wavelength band to be radiated onto the specimen formed with the wire pattern, from among the beams of the plurality of wavelength bands emitted from the light source means and at the same time selects, from among the plurality of optical systems, an illumination optical system that corresponds to the beam of the selected wavelength band.

According to another aspect, this invention provides a defect inspection apparatus comprising: a light source means for emitting beams of a plurality of wavelength bands; a light radiation means for selecting a beam of a desired wavelength from among the beams of the plurality of wavelength bands emitted by the light source means, adjusting a polarized state of the selected beam of the desired wavelength, and radiating the adjusted beam onto a specimen formed with a wire pattern; a detection means for receiving an optical image of the specimen, radiated with the beam of the desired wavelength from the light radiation means and formed with the wire pattern, and for outputting an image signal; an image processing means for processing the image signal output from the detection means to detect defects; and a control means for controlling the selection of the beam of the desired wavelength performed by the light radiation means and for controlling the adjustment of the polarized state performed by the light radiation means.

With this invention, it is possible to quickly select an optical condition that improves the grayscale depth of defects and reduces the grayscale depth of pseudo defects, thereby realizing a highly sensitive, high-speed inspection. It is also possible to find in short time a plurality of optical conditions that maximize the detection rate of desired DOI (Defects of Interest).

These and other objects, features and advantages of the invention will be apparent from the following more particular description of preferred embodiments of the invention, as illustrated in the accompanying drawings.

Other objects, features and advantages of the invention will become apparent from the following description of the embodiments of the invention taken in conjunction with the accompanying drawings.

DESCRIPTION OF THE EMBODIMENTS

Embodiments of this invention will be described in the following.

Embodiment 1

Figure 1:
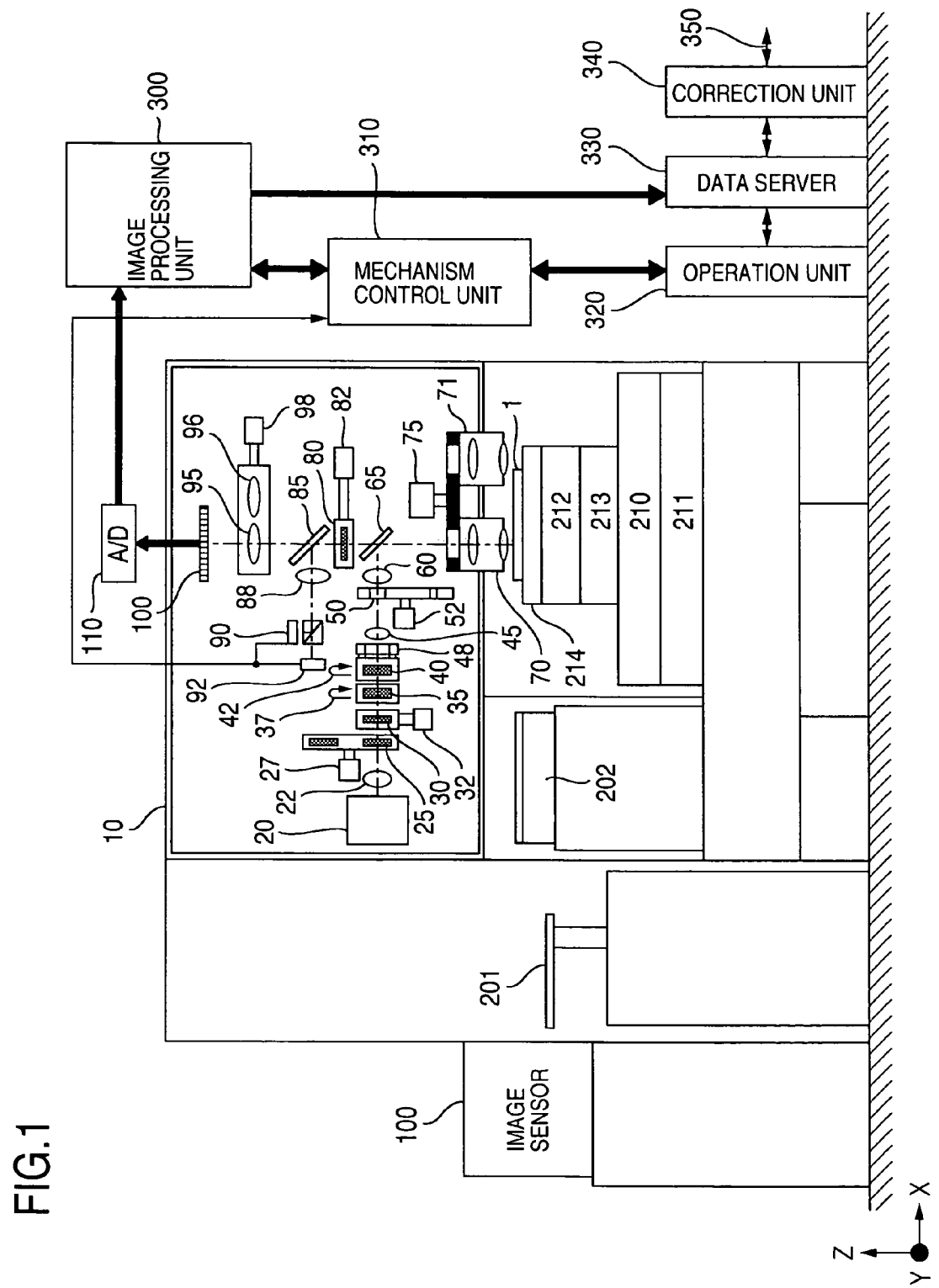
FIG. 1 is a front view showing an outline construction of an optical appearance inspection apparatus.

A basic construction of an optical defect inspection apparatus according to this invention is shown in FIG. 1. A wafer 1 is stored in a hoop 100 and loaded into a notch detection unit 202 by a wafer loader 201. The wafer 1, that has its notch detected by the notch detection unit 202 and is prealigned, is attracted to a wafer chuck 214 mounted on an X stage 210, a Y stage 211, a Z stage 212 and a θ stage 213. Above the wafer 1 is arranged an optical system 10 to detect an image of a wafer surface (this figure shows a construction of a bright field detection optical system using a falling light illumination). A light source 20 emits light of a wide wavelength band and may use such lamps as Xe lamp, ultrahigh pressure Hg lamp, Hg—Xe lamp and halogen lamp. Light from the lamp 20 passes through a lens 22, a wavelength selection filter 25 and a polarizer 30. The wavelength selection filter 25 is, for example, an interference filter or a colored glass having an absorbing band of a particular wavelength. The wavelength selection filter 25 comprises a plurality of filters with different penetration wavelengths arranged in a wavelength filter selection mechanism 27 so that the illumination wavelength can be changed.

The polarizer 30 improves a contrast of defects by using a polarized illumination. The light that has passed through the polarizer 30 becomes a linear polarization and then passes through a half waveplate 35 that rotates the orientation of oscillation, thereby controlling the oscillation direction of light to the one that improves the contrast of defects. The half waveplate 35 is mounted in a half waveplate rotation mechanism 37 that rotates the oscillation direction of the light that passes through it to a desired direction. To improve the rate of detection for various kinds of defects, an elliptically polarized illumination (including circular polarization with an ellipticity of 1) may be useful. So, a quarter waveplate 40 is also used for elliptical polarization. The quarter waveplate 40 is mounted in a quarter waveplate rotation mechanism 42 that changes the elliptical shape of the transmitted light into desired one. If a sufficient sensitivity can be obtained without using an elliptically polarized illumination, the polarizer 30 is not necessary. Thus, to prevent a loss of light quantity due to the polarizer 30, the polarizer 30 is mounted on a polarizer insertion/retraction mechanism 32 that removes the polarizer from an illuminating light path. The half waveplate and quarter waveplate are not required when a randomly polarized illumination is used. But when the specimen is made of quartz or magnesium fluoride, a transmissivity of 90% or higher can be secured, so they may be left installed without causing a problem of light quantity loss. Therefore, the half waveplate and quarter waveplate may be left installed in the light path or removed from it when a randomly polarized illumination is used.

The light that has passed through these optical elements forms an image of the light source at a position of a diaphragm 50 through a lens 45. Light then passes through the diaphragm 50 and a lens 60 and is reflected by a beam splitter 65 to fall on and illuminate the wafer 1 through objective 70. The diaphragm 50 is installed in a diaphragm selection mechanism 52 in which a plurality of diaphragms of different opening shapes and diameters are arranged. The diaphragm 50 may have a circular opening with a light axis at the center, a ring opening outside the axis, or 2- or 4-pole opening outside the axis. For a light path, a shape of diaphragm that is effective in improving the contrast of defects and reducing the pseudo defect contrast is selected from among a plurality of diaphragms installed. The image at the diaphragm 50 is projected onto the pupil of the objective to produce the Koehler illumination.

Of the beams that were reflected, diffracted and scattered by the pattern on the wafer 1, a beam that propagates within NA of the objective 70 is again captured by the objective 70. The beam that has passed through the beam splitter 65 now enters an analyzer 80 that passes only a particular oscillation component of an electric field vector, thus forming an image of the pattern of the wafer 1 on an image sensor 100 through an image forming lens 95. In the light path a beam splitter 85 is installed to produce a focus position detection beam that is used to detect a difference between a focus position of the objective 70 and the surface of the wafer 1. The detection of focus may, for example, involve projecting a stripe pattern 48 arranged in the illumination system onto the wafer 1 and introducing the projected image into the focus detection system. With respect to the stripe pattern image forming position (image plane in design) when the wafer 1 is at the focused point, two focus detection image sensors 90, 92 are arranged at defocused positions on the wafer side and on the opposite side.

By comparing contrasts of stripe pattern images detected by these image sensors 90, 92, a mechanism control unit 310 detects a positional relation between the wafer 1 and the focused position. When the wafer 1 is deviated from the focused position, the mechanism control unit 310 gives a command corresponding to the amount of deviation to the Z stage 212 to control the wafer 1 to the focused position. The image sensor 100 is, for example, a linear image sensor (including time delay integration type) and successively detects images of the wafer 1 by moving the X stage 210 at a constant speed. Image information from the image sensor 100 is converted by an A/D converter 110 into a digital image before being entered into an image processing unit 300.

The objective lens may be replaced according to the inspection speed and the contrast of defects to allow for an inspection that matches the user needs. For this reason, a revolver 75 is used to make it possible to replace the objective 70 with an objective 71 of a different NA and a different magnification factor.

The image processing unit 300 compares images of the same patterns in design to determine defect candidates. Representative methods for image comparison include a die comparison method that compares images of adjoining dies and a cell comparison method that compares images of adjoining memory cells. There are also other methods, such as one that compares design pattern data with an image detected by the image sensor and one that compares a reference image generated from a plurality of die images with sensor detected images to identify defect candidates. The information used by the image processing unit 300 to determine the defect candidates includes images of defective portions, reference images for comparison, difference images, coordinates, and image characteristic quantities calculated for image comparison and defect decision. These information are stored in a data server 330 and can be displayed by an operation unit. The operation of the entire inspection apparatus is directed by the operation unit 320, including the loading of the wafer 1, wafer θ alignment, setting of optical conditions, test inspections for condition determination, and normal inspections. For inspections of the wafer 1 for which an inspection recipe has already been prepared, an external automatic control is possible which is executed from a higher system that can communicate with the inspection apparatus. Further, information on inspection result can also be searched, extracted and displayed by the higher system. The inspection results can therefore be checked from outside (e.g., outside a clean room) without an operator being required to make various commands at the apparatus body.

Figure 8:
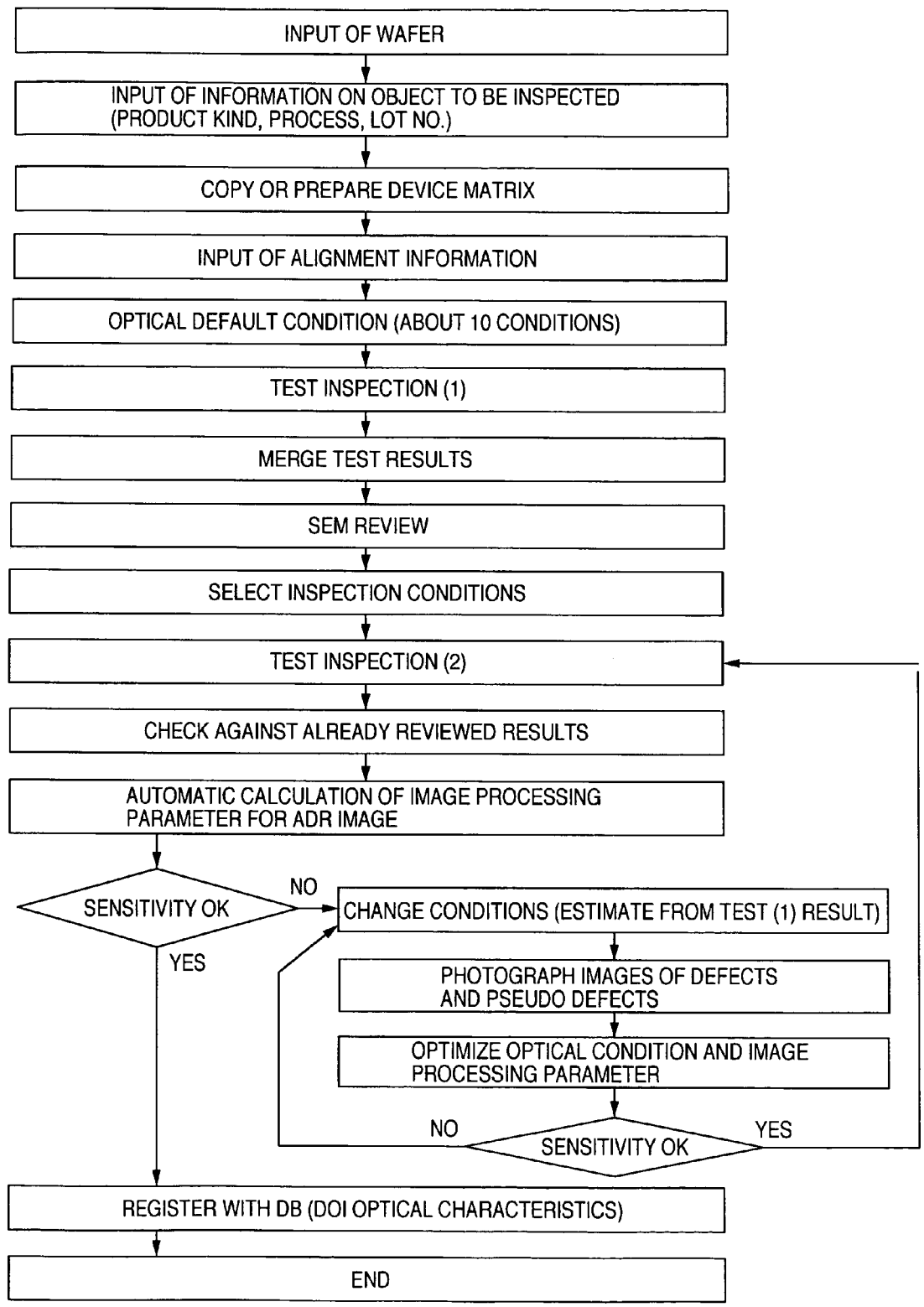
FIG. 8 is a flow diagram showing a flow of a test inspection.

The function and construction of the optical system have been described by referring to FIG. 1. As the number of functions and conditions increases, it becomes increasingly difficult to determine optical conditions and image processing conditions. An effective procedure for determining the optical conditions is shown in FIG. 8.

A wafer to be inspected is input into the apparatus and the wafer information is also entered. The information may include a kind of specimen, process and lot number. Next, an arrangement of dies formed on the wafer and memory cell areas in the dies (device matrix) are specified. If the device matrix is already prepared in other process, the already prepared device matrix is copied. Next, view fields of the wafer and the optical system, coordinate information for θ alignment with the XY stages, and a target mark for alignment are registered. Then, of the functions and conditions of the optical system, those conditions (about 10 conditions) under which various kinds of predetermined defects can easily be detected are used to execute test inspections [1]. The test inspections [1] are performed on a larger pixel size (size of one pixel of the image sensor on the wafer) than that used for actual inspections (also called a normal inspection) performed after the condition determination. When a certain area of the wafer is test-inspected, for example, it is possible with the above procedure to reduce the inspection time to (pixel size during test divided by pixel size during normal inspection), thus shortening an overall time required for the test inspection [1].

Next, defect candidates detected under all conditions are merged into one inspection result. At this time, it is noted that there are defect candidates that are detected under two or more inspection conditions. These candidates are handled as one defect candidate by checking their coordinates. At this time, information is left in the merged inspection result so as to be able to identify under what condition the defect of interest was detected. Based on the merged inspection result, a review is performed using a SEM (scanning microscope). From the SEM review result, a decision is made as to whether the defect of interest is a defect that should be allowed to be detected or a pseudo defect that does not have to be detected. Based on this review result, inspection conditions under which defects are easily detected and pseudo defects are not easily detected are chosen.

The selection involves using images and characteristic quantities of defects and pseudo defects obtained by the test inspection [1] under the default condition and optimizing a combination of image processing parameters that makes it easy to distinguish between defects and pseudo defects. A capability to distinguish between defects and pseudo defects when the optimized image processing parameters are used is calculated and, based on this calculated result, a combination of optical condition and image processing parameter which allows defects to be most easily detected and prevents the detection of pseudo defects is determined. Or, this result is displayed on the operation unit so that the apparatus user can select a desired combination of optical condition and image processing parameter. In this case, since a plurality of combinations of optical condition and image processing parameter are displayed, SEM images of defects and defect candidates detected under individual conditions may also be displayed to make the selection easy for the user.

Next, with the pixel size set to the one used during the normal inspection and with other optical conditions set to the automatically calculated or user-selected conditions, test inspections [2] are performed. The results of the test inspections [2] are checked against the SEM-reviewed defects and pseudo defects in terms of coordinates. By using images to be compared with the images of the checked defects and pseudo defects and also defect characteristic quantities obtained by the inspection, an image processing parameter that allows for the most reliable distinction between defects and pseudo defects is automatically calculated. Under this automatically calculated image processing parameter, information on defect candidates that were determined to be defects is displayed. The information to be displayed include SEM-reviewed images and information on defects/pseudo defects that were reviewed.

By using this information, decisions are made as to a) whether the user has a sufficient sensitivity and b) whether the rate of pseudo defects is within an allowable range. If the sensitivity and the rate of pseudo defects are not within the allowable range, an optical condition that enhances the sensitivity and one which lowers the rate of pseudo defects are estimated from among the optical parameters that were changed by the test inspections [1]. Under this condition, images of defects and pseudo defects and images of portions to be compared are photographed by a two-dimensional camera different from the image sensor that is used in the actual inspection (for example, an alignment camera 150 [black and white camera] shown in FIG. 2). This step is taken for the following reason. Since the image sensor 100 used for actual inspection is a linear sensor, when an image at particular coordinates is taken, the stage must move at a constant speed, making the image sensor take longer to photograph the image than the two-dimensional camera. However, for a user who considers the image taking time does not pose any problem, the linear image sensor 100 may be used. Particularly when the image sensor 100 and the alignment camera 150 have greatly differing light separation sensitivities and pixel sizes, it is safe to use the image sensor 100 in photographing the images.

Next, by using the images taken of the defects and pseudo defects, an optical condition and an image processing parameter that result in the most desirable sensitivity and pseudo defect rate are calculated. Then, with the optimal optical condition and image processing parameter, an automatic calculation is performed to see if the sensitivity of detecting target defects and the pseudo defect rate are permissible or not. If they are within an allowable range, this optimal condition is used to perform the test inspection with the pixel size that is used in the normal inspection. If they are outside the allowable range, it is possible to change the optical condition again, take images of the defects/pseudo defects and of portions to be compared and then improve the optical condition and the image processing parameters.

The results of the second test inspection that was done at the pixel size used in the normal inspection are checked against the SEM-reviewed results to improve the image processing parameters as required. When any improvement is made, the inspection sensitivity and pseudo defect rate are checked. If there is no problem, the condition determination step is completed and information on SEM-reviewed defects (e.g., defect sizes, classification results, and causes of defects) are registered with database. This database will be used for future condition determination steps for semiconductor wafers that use the same product kind, the same process or the same semiconductor material. It is highly likely that the results of test inspections at the pixel size used in the normal inspection may include defects that are not SEM-reviewed. When it is desired to check if the defects not SEM-reviewed are defects that one wants detected or pseudo defects, it is possible to perform the SEM review on these defects for confirmation. For efficient performance of the SEM review, in highly reliable categories where defects are accurately classified by using the results of automatic classification by the inspection apparatus, only representative defects may be SEM-reviewed.

Figure 9:
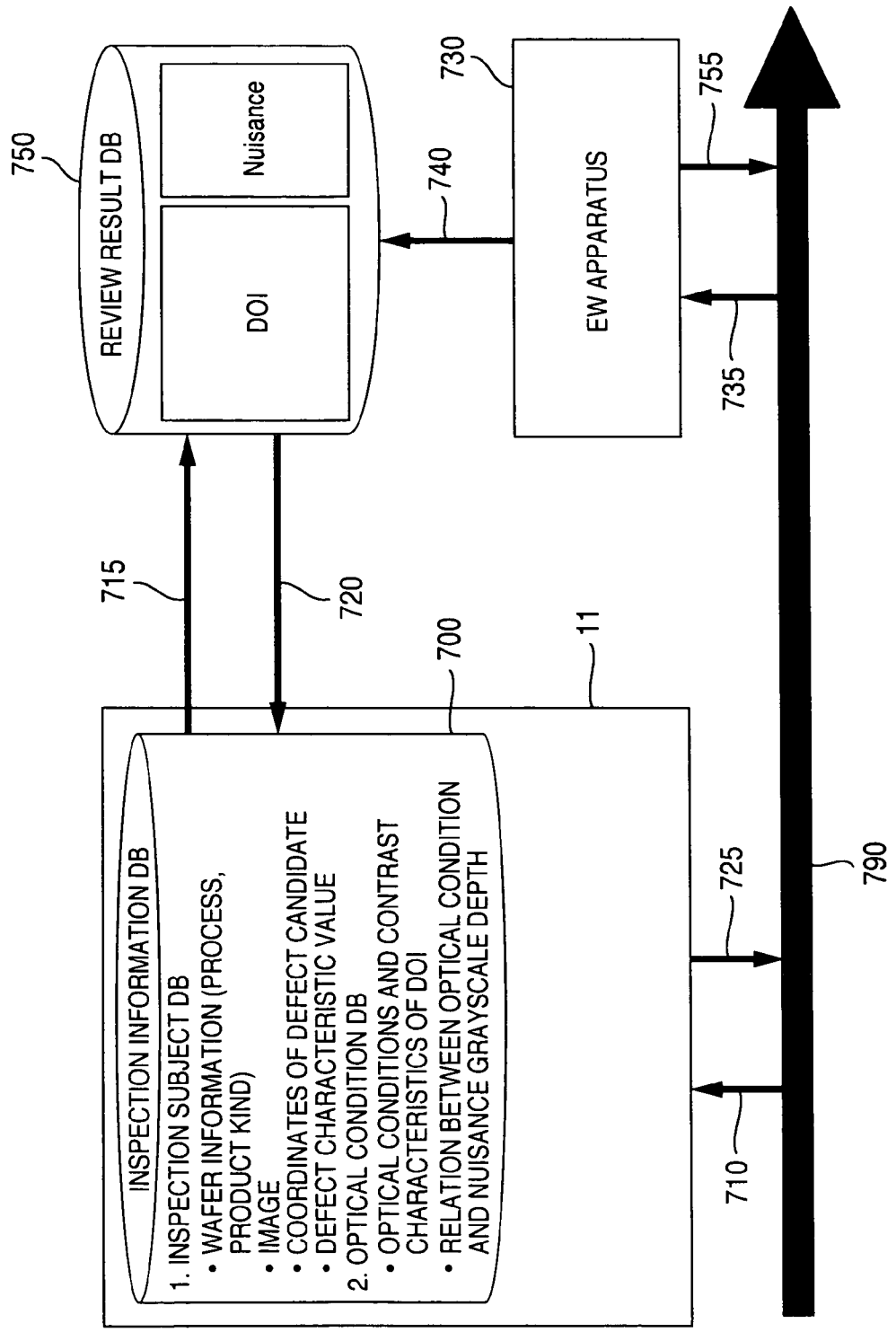
FIG. 9 is a block diagram showing a configuration of an inspection system including a review device.

Particularly when performing an inspection condition determination step, the results of test inspection need to be checked against the results of review performed by the SEM review device 730. As shown in FIG. 8, if the SEM review results can be displayed on the inspection apparatus 11 for confirmation, the process of inspection apparatus condition determination can be done efficiently. A combined system of the inspection apparatus 11 and the review device 730 for this purpose is shown in FIG. 9. A wafer 1 used for condition determination is input (710) into the inspection apparatus 11 and then information on the wafer 1 is also input. By using this information, an inspection information database (hereinafter referred to as inspection information DB) 700 is searched to extract the result of past inspection that was performed on the same kind of product of preceding generation using the same process.

To determine from the extracted result a representative defect that affects yield, information on the extracted inspection result (kinds, process, lot number, defect coordinates, etc.) is sent (715) to the review result DB (it may or may not be incorporated into the review device). And the review result DB returns review images, their classification result, analysis of the result and information on countermeasures to the inspection information DB of the inspection apparatus 11 (720). The operator checks the returned information at the inspection apparatus and selects defects that affect the yield and those required to be detected for the process monitoring. For pseudo defects also, the operator checks the review images at the inspection apparatus and specifies them as the defects that he or she wants undetected.

For the defects that the operator wants detected and for the pseudo defects that he wants left undetected, a search is made for optical condition that was used when these defects were detected during past inspections and for defect information (such as grayscale depths, defect characteristic quantities and images) and also for information on condition determination process when these defects were detected (optical condition in the condition determination process and contrast characteristics of defects and pseudo defects; e.g., waveforms and contrast characteristics of defects and pseudo defects, polarization filtering and contrast characteristics of defects and pseudo defects). From this search result, an optical condition is estimated under which defects and pseudo defects can be distinguished highly reliably and, under this condition, a test inspection is performed. By taking full advantage of the past inspection information and past condition determination information, the condition determination process for wafers with fine design rules is performed efficiently. This is effective in narrowing down the default test inspection conditions shown in FIG. 8, offering an advantage of being able to shorten the test inspection time.

The above process concerns the narrowing down of the test inspection information by using past inspection results and, under the narrowed-down condition, an actual test inspection is performed. For defect candidates that are picked up by the test inspection, the wafer 1 is temporarily taken out of the inspection apparatus 11 (725) and loaded into the review device 730 (735). In the review device 730, the defect candidates are reviewed and a decision is made as to whether the defect candidates are defects that the operator wants detected or pseudo defects that he wants left undetected. The review result is transferred to the review result DB where it is stored (740). If the detection sensitivity and the pseudo defect rate are bad, the wafer 1 is taken out of the review device (755) and again input into the inspection apparatus to adjust the inspection condition. After the adjustment is made of the inspection condition, the result of the test inspection is checked against the coordinates of the already reviewed defects to decide whether the pseudo defect rate is permissible or not. For new defects that are detected after the inspection condition has been adjusted, there are no review results. So, only the defect candidates that have not been reviewed are subjected to a review by the review device and the result is stored in the review result DB.

Figure 10:
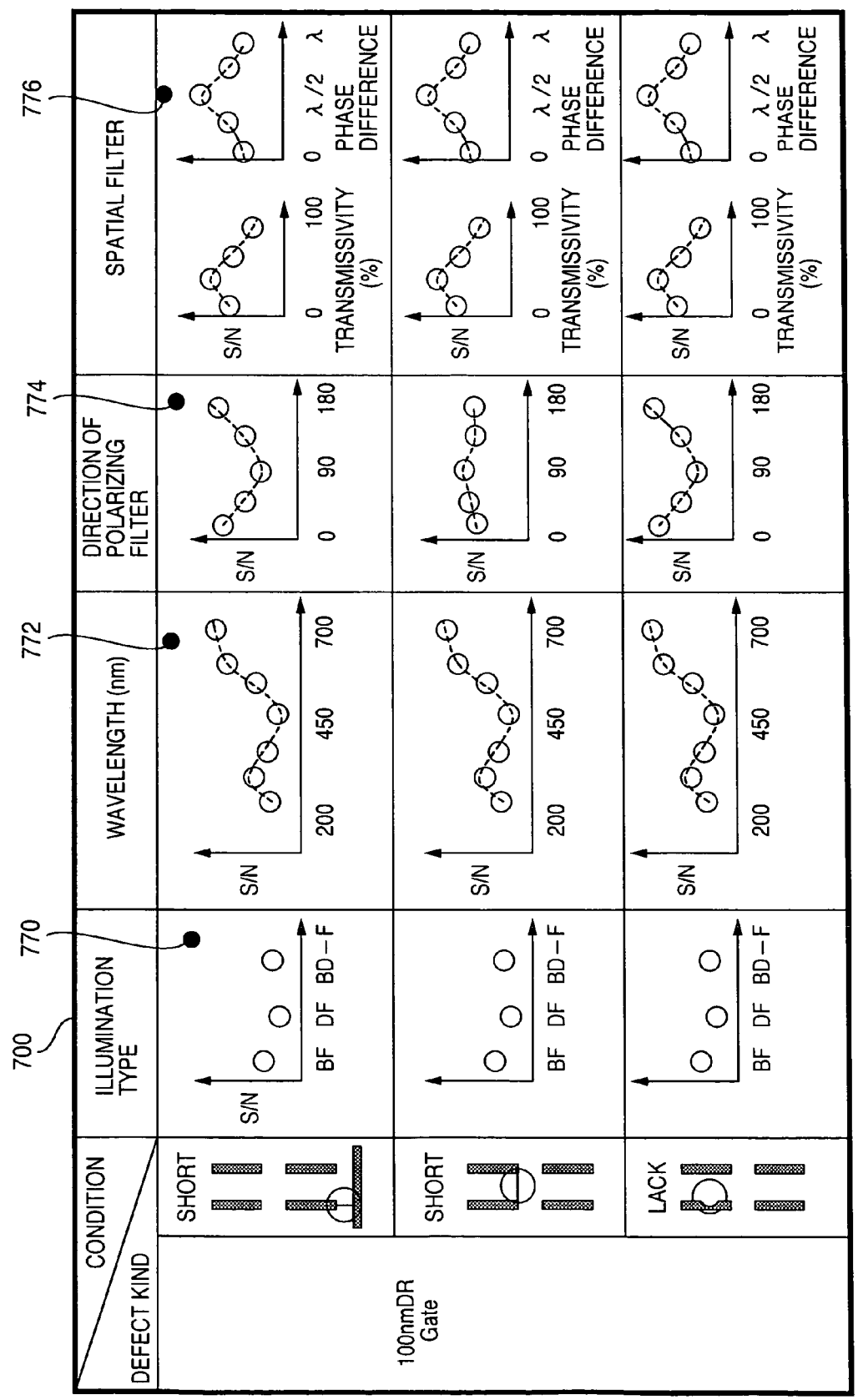
FIG. 10 is a diagram showing an inspection information database in the form of table.

A process of accumulating the condition determination results for wafers in an inspection information database 700 is shown in FIG. 10. The condition determination involves finding where defect candidates are by the test inspection of FIG. 8, and reviewing the defect candidates to see if they are defects or pseudo defects. If, for example, a defect candidate of interest is found to be a defect, a bright field and dark field of defect and its portion to be compared and a bright/dark field image are detected to determine the illumination type (770). The construction of an optical system to detect the bright field/dark field and the bright/dark field image will be detailed by referring to FIG. 7 of embodiment 2. For example, the bright field image and dark field image may be detected and combined together to estimate a bright/dark field image. From these images, a grayscale depth of the defect portion is calculated. Based on these, an illumination type which is advantageously used for defect detection is selected.

Then, light-separated images of the defect portion and its portions for comparison are detected (772). The images are detected by changing the wavelength in steps of 30-60 nm. Using the detected images, a comparison inspection is performed to determine the grayscale depth of the defect portion. At this time, provision is made so that the polarity of grayscale depth (indication of whether the portion of interest is dark or bright with respect to the normal portion) can be identified at each wavelength. Also for the polarization filter, the filter transmissivity and defect grayscale depth are similarly calculated (774). Also for spatial filter, the filter portion's transmissivity and its grayscale depth characteristic with a phase difference taken as parameter are accumulated (776). As to the relation between the optical conditions and the defect grayscale depth, two or more characteristic defects (e.g., shorted defects, open defects, debris and voids) are chosen and their relations between optical condition and defect grayscale depth are accumulated. Similarly, for the pseudo defects, the relations between optical condition and grayscale depth are stored in the database.

An example of the first step to select the inspection condition that is advantageous for the inspection sensitivity involves extracting a condition that makes the defect grayscale depth relatively large. An example of the second step involves extracting a condition that makes the grayscale depth of pseudo defect relatively small. Since the overlapping condition of these conditions tends to increase the inspection margin (=(defect grayscale depth)−(pseudo defect grayscale depth)), this condition may be recommended as the inspection condition to the operator so that he or she can accurately determine the inspection condition conducive to high sensitivity. If a wavelength range or width is narrow, the grayscale depth of pseudo defects increases due to thin film interference, which may in turn result in little or no inspection margin being left under any optical conditions.

When there is no inspection margin or it is desired to increase the margin, a check is made to see if the pseudo defect portion is dark or bright relative to the normal portion. For example, if the pseudo defect portion is darker, a wavelength that makes this pseudo defect bright is picked up. Illuminating the wafer with light including the extracted wavelength can average the brightness of the pseudo defect portion, reducing the grayscale depth of the defect portion, thereby increasing the inspection margin. At this time, rather than focusing only on the pseudo defect portions, it is necessary to make sure that when light of multiple wavelengths is radiated, the reduction in the grayscale depth of the defect portion is not smaller than the reduction in the grayscale depth of the pseudo defect. This makes it possible to select a condition under which the defect margin can be increased by radiating two or more wavelengths of light simultaneously.

In the above, the method of selecting a wavelength that results in a high inspection margin has been explained. The same also applies to the polarization filter and spatial filter. For example, the grayscale depths of the defect portion and the pseudo defect are compared to determine a condition that results in the largest margin. It is likely that detecting all kinds of defects one wishes to detect under a single optical condition is difficult. In that case the same wafer may be inspected under two different conditions. For the selection of these two conditions to maximize the rate of detecting a variety of kinds of defects, this database can also be utilized.

Figure 4:
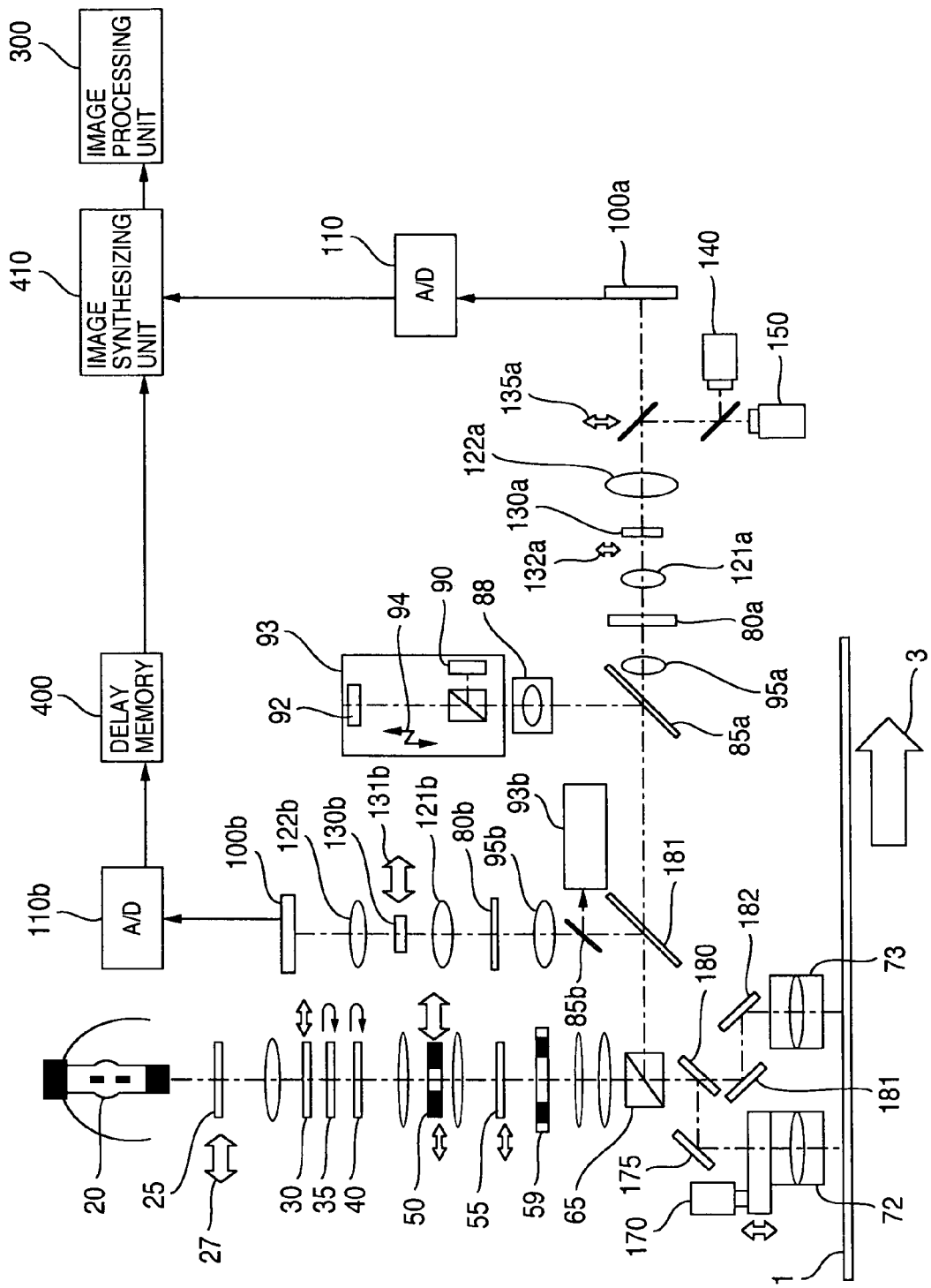
FIG. 4 is a front view showing an outline construction of a variation of the optical system of the optical appearance inspection apparatus.
Figure 6:
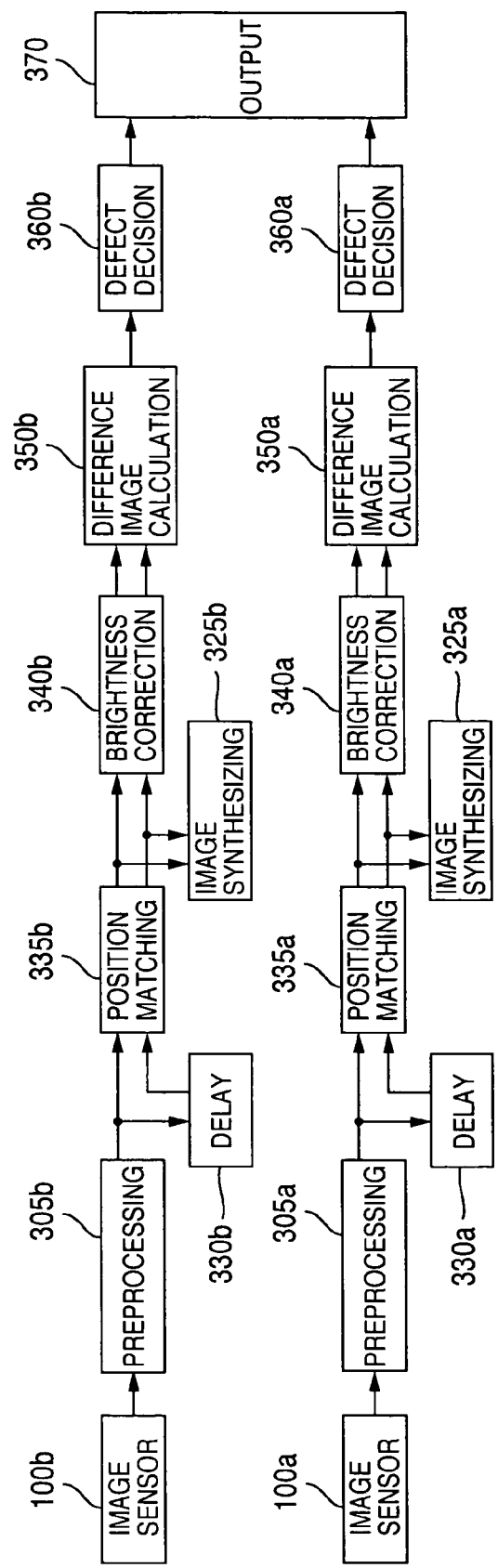
FIG. 6 is a block diagram showing a flow of signal processing to explain about another example of an image processing function.

In the above, the optical system with the construction of FIG. 4 has been described to detect the images of two objective lenses that are aberration-corrected in two bands and to perform the image combining processing. Now, a construction will be explained which simultaneously detects two kinds of images having different conditions for the polarization filter (analyzer) and spatial filter. Only one objective is used and a beam splitter is installed which exhibits a uniform reflectivity characteristic for an illumination wavelength when a dichroic mirror is selected in the detection system. In one detection light path and another detection light path, the condition of at least one of the polarization filter and the spatial filter is changed. Each of these detection light paths is so constructed as to allow a bandpass filter to be installed therein. With this arrangement the wavelength detected can be changed by the image sensor [1] and [2]. The images detected by these image sensors are independently processed as shown in FIG. 6. As a result, the inspections under two conditions that maximize the detection rate of various kinds of defects can be performed in one inspection, enhancing the throughput by two times.

The method of narrowing down the test inspection conditions using the inspection information DB 700 will be described. A wafer 1 used for determining a condition is loaded into the inspection apparatus 11 and the wafer information (process, product kind, construction, line width, etc.) is entered (323). Inspection conditions for wafers having the same or similar process, product kind and construction as the wafer 1 used for condition determination, as well as grayscale depth characteristics of defects and grayscale depth characteristics of pseudo defects, are sent to an optimum optical condition estimation unit 780. Based on the past grayscale depth characteristics of defects and pseudo defects that have been received, the structure of the wafer used for condition determination and a pattern line width are entered. Then the optimum optical condition estimation unit estimates, according to preset equations, how the contrast and grayscale depth of the pattern change when the line width shrinks, depending on the optical conditions. This estimation is done based on the past relationship between optical conditions and defect grayscale depths. This estimation is performed for each wavelength, diaphragm, polarization filter and spatial filter to estimate the optimal optical condition when the line width shrinks. The estimated, optimal optical condition is sent to the operation unit 320 (321). This condition is then specified as the test inspection condition shown in FIG. 8 to the optical system 10. As a result, the optical system can narrow the test inspection conditions, reducing the test inspection time.

A key to determining which condition is optimal is a condition that satisfies both a condition that makes the defect grayscale depth relatively large and a condition that makes the pseudo defect grayscale depth relatively small. An overlapping part of these conditions is a condition that increases the inspection margin. This condition is recommended as the inspection condition to the operator. So, the operation is now able to predict an inspection condition that produces a high sensitivity. As explained in FIG. 10, when a wavelength range or width is narrow, the grayscale depth of pseudo defects increases due to thin film interference, which may in turn result in little or no inspection margin being left under any optical conditions.

When the inspection margin is virtually nonexistent or when it is desired to increase the margin, a check is made of a condition that makes the pseudo defect portion darker than the normal portion and of a condition that makes it brighter. Illuminating the wafer with light including the extracted wavelength can average the brightness of the pseudo defect portion, thereby reducing the grayscale depth of the defect portion, thereby increasing the inspection margin. At this time, rather than focusing only on the pseudo defect portions, it is necessary to make sure that when light of multiple wavelengths is radiated, the reduction in the grayscale depth of the defect portion is not smaller than the reduction in the grayscale depth of the pseudo defect. This makes it possible to select a condition under which the defect margin can be increased by radiating two or more wavelengths of light simultaneously.

Figure 12:
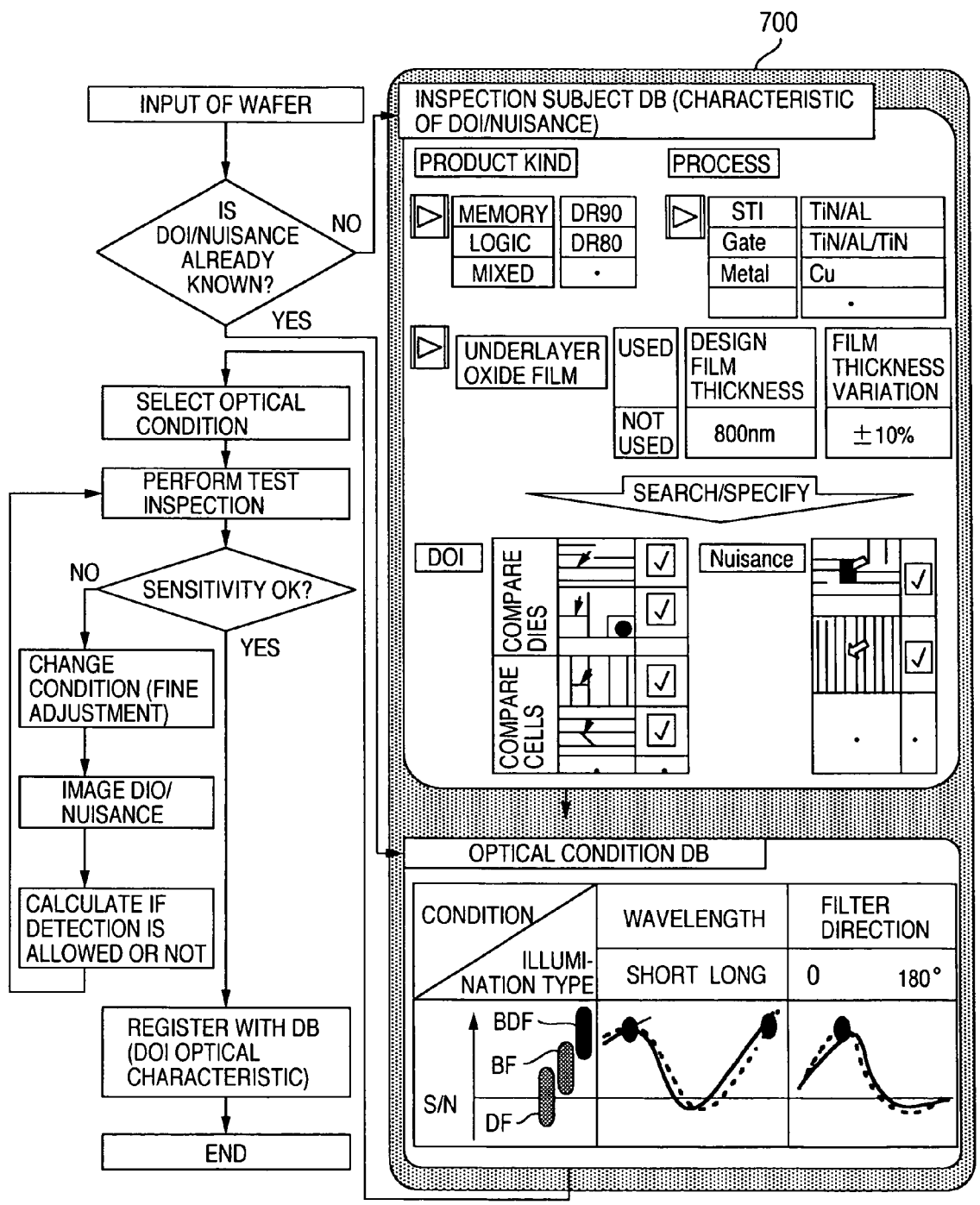
FIG. 12 is a flow diagram showing a basic flow of condition finding procedure.

FIG. 12 shows a basic flow for condition determination and an example of a condition determination screen in the operation unit. A wafer 1 is input to the inspection apparatus and a check is made as to whether coordinates of defects and pseudo defects are already known. For example, when defects are found during a demonstration of selection of apparatus or during inspections by other devices, the coordinates of these defects may be known. However, during a routine condition determination process in a semiconductor production line, the coordinates of defects are not known. In this case, the kind of product is first selected and its design rule specified. Next, a process is entered and then a material and structure of the pattern to be inspected are also entered. At this time, if the pattern is made in the form of thin film, a film thickness of the pattern is also entered in order to determine a reflectivity of the pattern.

Next, to check the thin film interference effect caused by an underlayer oxide film that is likely to be detected as the pseudo defect, the presence or absence of an underlayer is also entered. If there is an oxide film, its design film thickness, a design value and an empirical value of film thickness variations are also entered. Next, SEM review images of defects and pseudo defects that were inspected in the past and which were detected in the same or similar product kind and process are displayed from the inspection information DB. Of these images, defects that the operator wishes to detect in the wafer being inspected are specified. Also for the pseudo defects, the operator specifies defects that he or she wants left undetected. Next, an optical condition that makes the grayscale depth of specified defects large and the grayscale depth of pseudo defects small is recommended from the optical condition DB in the inspection information DB. When two or more conditions are recommended, all or particular conditions are selected and the test inspections are performed under the selected conditions. If a plurality of test inspections are performed, their test results are merged into a single test result, as in FIG. 8, and then SEM-reviewed to check the adequacy of the sensitivity. When the sensitivity is not enough, the optical condition is changed. At this time, as a clue for changing the optical condition, a relation between the grayscale depths of defects and pseudo defects in the optical condition DB is used.

Next, images of comparison portions of the defects and pseudo defects are taken. The sensors used to take these images are either a linear image sensor 100 used for normal inspection or a two-dimensional camera 150 used for alignment. Based on the detected images, the image processing parameters are optimized and then the image processing is performed to see if only the defects can be detected after optimization. From the result of this processing, a condition that provides the largest inspection margin is selected and the test inspection is performed again. If the result of inspection shows that the sensitivity is within an allowable range, the condition determination process is ended and the result of the condition determination as well as its process is accumulated in the optical condition database. The accumulated information will be utilized for future condition determination process for a shrunk pattern.

Figure 13:
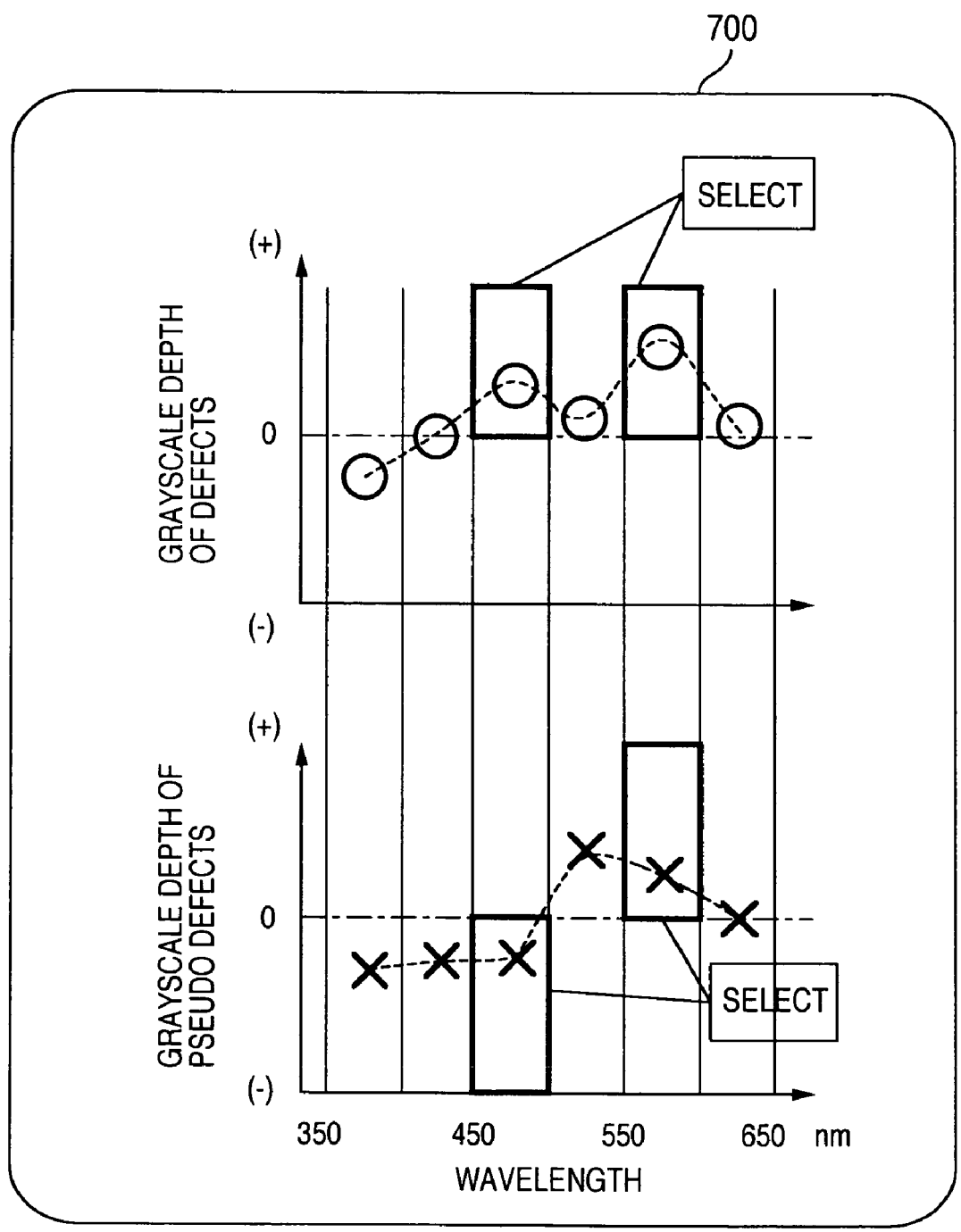
FIG. 13 is a graph showing relationships between illumination wavelengths and grayscale depths of defects and pseudo defects.

Decision criteria for determining an optimal wavelength condition, based on the result of test inspections that are performed by changing the wavelength band, are shown in FIG. 13. An abscissa in FIG. 13 represents a wavelength of illuminating light. The information on the test inspection is stored in the inspection information DB 700 together with the result of review-based decisions as to whether a defect candidate is a defect or pseudo defect. The inspection information DB 700 stores grayscale depths of multiple defects and pseudo defects detected by the test inspection for each wavelength of illuminating light used in the test inspection. Although FIG. 13 shows only representatives defect and pseudo defect, the actual inspection information DB stores the grayscale depths for all defects and pseudo defects detected by the test inspection. Based on these information, a wavelength condition that realizes a highly sensitive inspection meets the following two conditions:

[1] as for defects, a wavelength condition under which grayscale depths have the same sign and relatively large absolute values (e.g., simultaneous illumination of wavelengths 450-500 nm and 550-600 nm); and

[2] as for pseudo defects, a wavelength condition under which summing wavelengths results in a reduced grayscale depth (e.g., a minus wavelength of 450-500 nm and a positive wavelength of 550-600 nm which, when added together, will cancel the grayscale depths of the detected images). (These two conditions do not need to be met completely but are only required to make inspection S/N relatively high.) In this example, simultaneous illumination of wavelengths of 450-500 nm and 550-600 nm can secure the sufficient grayscale depth for defects and suppress the grayscale depth for pseudo defects, allowing for a highly sensitive inspection.

While FIG. 13 of this embodiment shows an example case where the wavelength is divided for test inspections, this method can also be applied to the illumination type selection (bright field, dark field and combined illumination of bright/dark fields), polarization filtering condition, spatial filtering condition, illumination σ condition (including conditions for diaphragm outside axis), and focus offset condition. That is, for these items of conditions, test inspections are performed under a plurality of conditions and the test results are stored in the inspection information DB 700. It is therefore possible to determine from the stored information a condition conducive to enhancing the sensitivity. Further, while FIG. 13 focuses on the polarity and absolute value of grayscale depth, the above method is effectively applied to optimizing characteristic quantities other than the grayscale depth by determining image characteristic quantities, such as sizes of defects and other image processing parameters, and a relation between defects and pseudo defects. As an example configuration that moves the above method a step further, it is possible to automatically calculating optimum values of optical conditions and image processing conditions, based on the inspection information DB 700.

[Variation 1]

Figure 2:
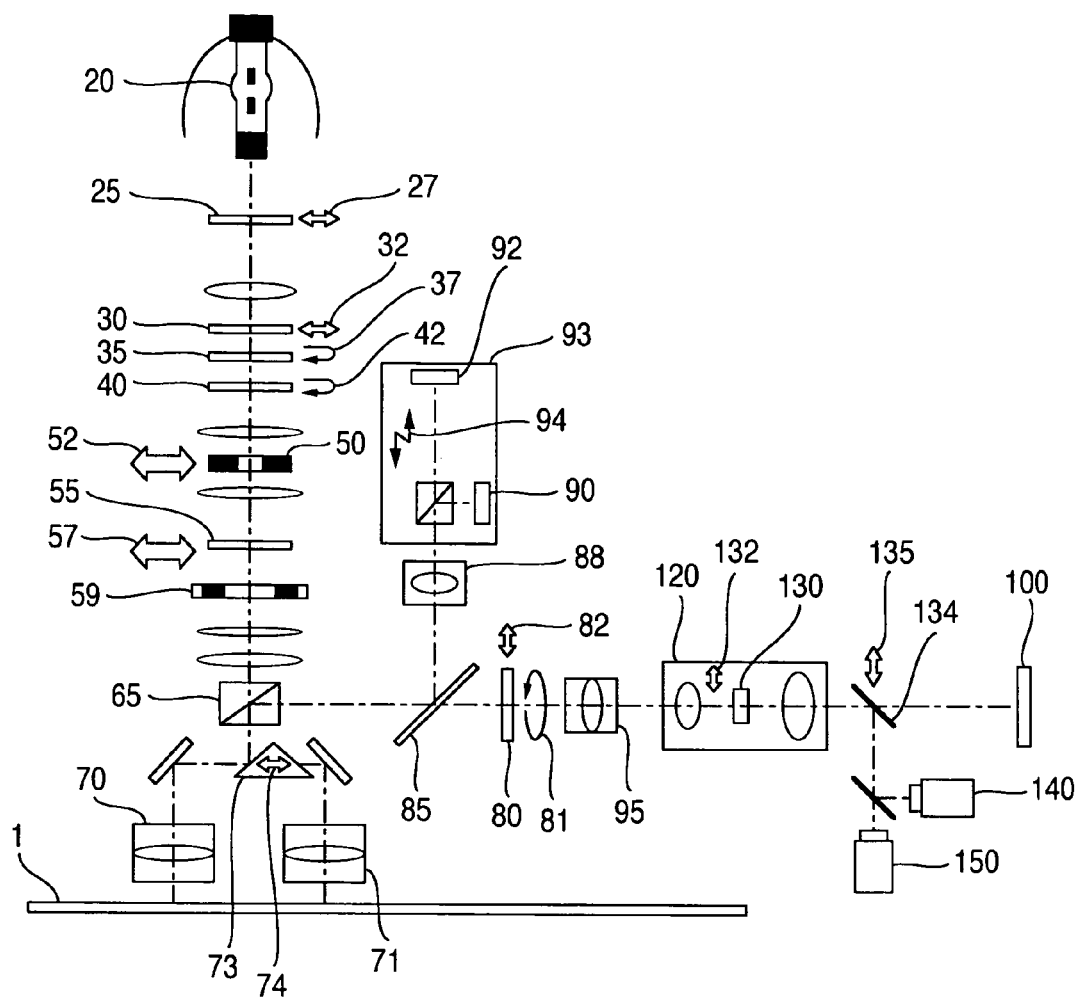
FIG. 2 is a front view showing an outline construction of an optical system of the optical appearance inspection apparatus.

A first variation of the optical system explained in the first embodiment is shown in FIG. 2. Light from a light source 20 has its illumination wavelength selected by a wavelength selection filter 25. The wavelength selection filter 25 comprises a plurality of filters with different spectral transmittances that are mounted on a wavelength filter selection mechanism 27. In an illumination path is installed a polarizer 30 that passes only an electric field vector with a particular direction oscillation. As for the direction of oscillation, a defect contrast is improved effectively by setting the direction of oscillation mainly parallel to a defect or a pattern close to the defect. However, the direction of oscillation conducive to the improvement of the defect contrast changes depending on the material and structure of pattern and defect. For this reason, a half waveplate 35 to rotate the orientation of oscillation of light that has passed through the polarizer 30 is used to control the oscillation direction of light to the direction that improves the contrast of defects. This half waveplate 35 is mounted on a half waveplate rotation mechanism 37 that rotates the oscillation direction of the light to a desired direction as it passes through the waveplate.

In improving the rate of detection for various kinds of defects, an elliptically polarized illumination (including circular polarization with an ellipticity of 1) may be useful. So, a quarter waveplate 40 is also used for elliptical polarization. The quarter waveplate 40 is mounted in a quarter waveplate rotation mechanism 42 that changes the elliptical shape of the transmitted light into desired one. The light that has passed through these optical elements forms an image of the light source 20 at the position of the diaphragm 50 through a lens. The diaphragm 50 is installed in a diaphragm selection mechanism 52 in which a plurality of diaphragms of different opening shapes and diameters are arranged.

Next, if there are variations in reflectivity of the wafer 1 or a luminance fall in the light source 20, the detection light quantity at the same position on the wafer 1 needs to be kept constant. Therefore, a ND (Neutral Density) filter 55 to adjust the illumination light quantity is provided. This ND filter 55 comprises a plurality of filters of different transmittivities. For example, a plurality of ND filters 55 are arranged along the circumference of a disklike plate, as with the wavelength filter selection mechanisms 27 of FIG. 1. They are mounted to a mechanism 57 that rotates this plate by an electric motor to place an appropriate ND filter 55 in the light path. (Other selection mechanisms for optical components may include one which arranges a plurality of components and filters on a motor-driven linear stage and moves an appropriate component and filter into the light path.)

After passing through the ND filter 55, light illuminates a stripe pattern 59 for auto focus (AF) situated at a conjugate position with the wafer 1 to form an image of stripe pattern on the wafer 1 through the lens and objective 70. A detection light reflected from the wafer 1 is reflected by a beam splitter 65 and split by a beam splitter 85 into an AF light path and an image detection light path. In the AF light path an image forming lens 88 focuses the image of the stripe pattern 59 projected onto the wafer 1. Two AF image sensors 90, 92 are located a predetermined distance from this image plane on the wafer side and on the opposite side. From the contrast of the stripe pattern image detected by the two sensors 90, 92, the focus state of the wafer 1 is detected.

The wafer 1 is formed of a multilayered film and the focus of the objective 70 needs to be aligned with the layer being inspected. Therefore, the method of offsetting the wafer 1 in the Z direction to realize the AF function involves moving the AF image sensors 90, 92 a predetermined distance along the optical axis direction, then fixing them, and controlling the wafer 1 in the Z direction so that the contrasts of the stripe pattern images detected by the two sensors 90, 92 are equal. For this purpose, the AF image sensors 90, 92 are mounted on the stage 93, which is preferably slid in a direction parallel to the optical axis by a drive mechanism 94. It is also desired that the stripe pattern 59 be moved in the direction of optical axis so that the stripe pattern can maintain its conjugate relation with the offset wafer 1.

The light that has passed through the beam splitter 85 and is introduced into the image detection light path enters the analyzer 80 which allows only an electric field vector that oscillates in a predetermined direction to pass. The light transmission axis of the analyzer 80 is adjustable because the direction conducive to enhancing the contrast changes according to the material and structure/dimension of the defects and the positional relation with a nearby pattern. Thus, the analyzer 80 is mounted on a rotatable mechanism 81. The light that has passed through the analyzer 80 forms an optical image of the wafer 1 once through the image forming lens 95. This image is projected onto the image sensor 100 through a zoom lens 120. The zoom lens 120 is provided with a position conjugate with a pupil of the objective 70. At this position a spatial filter 130 can be installed. The spatial filter 130 comprises a plurality of filters with different shapes, transmissivities and phases. There is also a mechanism 132 that can set a desired spatial filter 130 conducive to an enhanced contrast of the defects.

The optical system is mounted with a defect review camera 140 and a wafer alignment camera 150. The defect review camera 140 is used mainly to determine conditions for inspection recipe. The alignment camera 150 is used to detect the θ alignment between the wafer 1 and the XY stages 211, 210 after the wafer 1 is loaded, and also to detect the relation between the field of view of the optical system and the coordinates of the wafer 1. Therefore, a mirror drive mechanism 135 is provided to bring a mirror 134 into the light path only when the light path is switched to the review camera 140 side and to the alignment camera 150 side. When a sufficient defect contrast is obtained with only the polarized illumination, the analyzer 80 may be removed from the light path to reduce a loss of detection light quantity. Thus the analyzer 80 may be mounted on a mechanism 82 that removes it from the light path. Further, if a sufficient defect contrast is obtained even without the polarized illumination, the polarizer may also be mounted on a mechanism 32 that removes the polarizer from the light path in order to improve the illumination efficiency. If the polarizer 30 is provided with a rotating mechanism, the oscillation direction of illumination can be set to a desired direction even when the half waveplate 35 installed in the illumination system is omitted. Thus, the half waveplate may be replaced with the rotating mechanism-mounted polarizer.

There is a call for high-speed inspection from the user of the inspection apparatus. This demand may be met by reducing the magnification of the objective lens to increase the field of view on the wafer 1 that can be imaged by the image sensor 100. Further, the defect contrast changes with wavelength. If the wavelength range is too wide for a single objective lens to correct aberrations, two kinds of objective may be used to totally cover the aberration correction range. This arrangement allows for an aberration correction over a wide range of wavelength, from ultraviolet to a long wavelength side of visible light (e.g., 360-700 nm).

Replacing the objective according to the inspection speed and the defect contrast allows for an inspection that matches the user needs. In the embodiment 1, the revolver 75 is used to allow the objective 71 to be replaced with another objective 70. This arrangement, however, increases the size of the objective depending on the wavelength used by the objective and the aberration correction accuracy. Another problem is that replacing the objective by the revolver 75 deteriorates the precision of repositioning of the objective lens. To cope with this situation, a proposed method may involve providing two kinds of objective, such as objective 70 and objective 71, fixing these objectives, and constructing a mechanism 74 which causes a horizontal moving mechanism 74 to move a mirror 73 of a right triangle disposed above the objectives so that the illumination light is incident on only one of the objective. With this arrangement, it is possible to change the magnification and aberration correction range (illumination wavelength) from the wafer 1 to the image sensor 100, with the objectives 70, 71 held immovable.

A step of processing images detected by the image sensor 100 and the subsequent steps are the same as those of embodiment 1.

[Variation 2]

A second variation of the optical system explained in the first embodiment will be described as follows.

Figure 3:
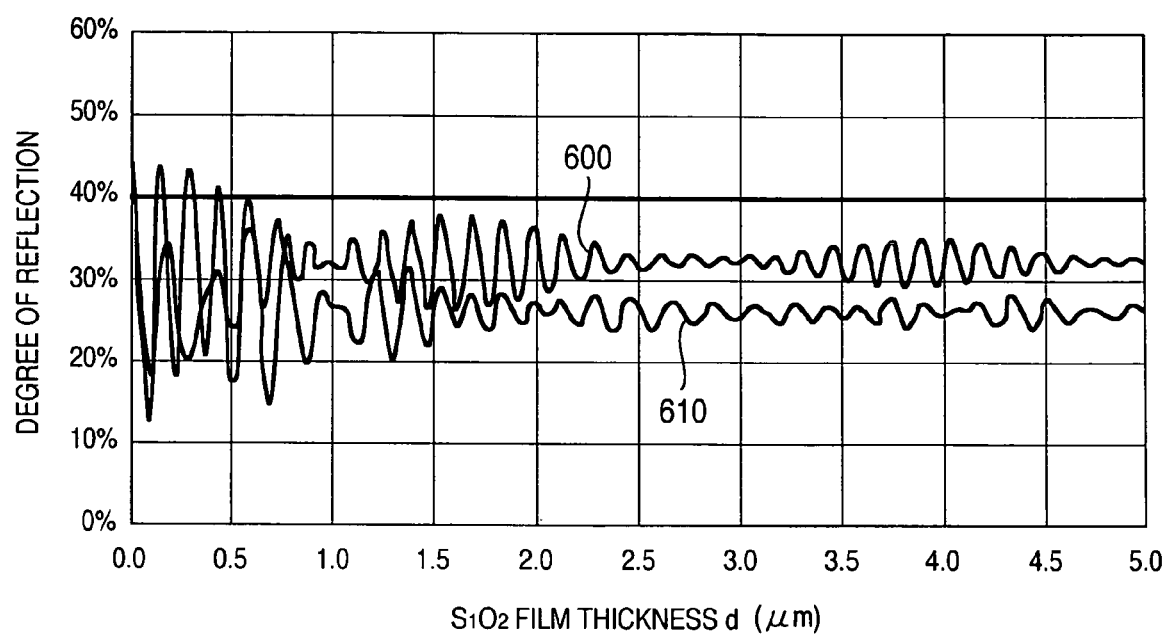
FIG. 3 is a graph showing a relationship between a thickness of SiO2 film and a reflectivity to explain about brightness variations caused by thin film interferences.

Pseudo defects that impair the inspection sensitivity are explained. A typical example of pseudo defect is a brightness difference between detected images which corresponds to a difference in interlayer insulation film thickness between dies being compared. FIG. 3 shows a relation between a SiO2 film thickness and a reflectivity in a model in which a SiO2 interlayer insulating film is deposited on the Si wafer. The illumination light has NA of 0.8 and calculations were performed for a 2-wavelength illumination 600 of 405 nm+436 nm and for a wide band illumination 610 of 405-587 nm. As the SiO2 film thickness changes, the reflectivity also changes due to the thin film interference.

This tendency becomes more distinguished as the wavelength band narrows. So, if there is a thickness difference in the SiO2 film between the dies whose images are being compared, the detected images have greatly differing brightnesses when a narrow-band wavelength illumination is used. The narrow-band wavelength illumination requires setting the default decision threshold larger than the difference image compared, giving rise to a possibility of fine defects being unable to be detected. To minimize brightness variations caused by thin film interferences, it is therefore advantageous to adopt a wide-band wavelength for illumination light. Adopting a wide-band wavelength illumination makes the aberration correction of the optical system more difficult. It is therefore desirable to meet both requirements—a required wavelength that allows defects to be detected with high contrast and a wavelength band or width that minimizes thin film interferences.

Conditions for illumination wavelength under which defects are detected with high contrast are as follows:

(1) In terms of resolution, a short wavelength illumination is advantageous. DUV (Deep Ultraviolet) and UV range wavelengths are desirable. As for the wavelength width, the presence of a wavelength width or band equivalent to the shortest wavelength is advantageous in terms of inspection S/N.

(2) Spectral transmittances that depend on the material and structure of patterns to be inspected need to be considered. For example, if a pattern of low reflectivity is formed over an underlayer of low reflectivity, a sufficient pattern contrast cannot be obtained. If a defect of low reflectivity (e.g., foreign matter) exists over a dark pattern, the defect has a low contrast. To be able to detect a defect with high sensitivity, it is necessary to prepare a wavelength that allows the defects to be detected with a higher contrast. In the case of aluminum wires, for example, they sometimes are coated with TiN on the surface, which exhibits a characteristic that its reflectivity increases in the wavelength range of 450-500 nm. Therefore, the wavelength that enables defects to be detected with high contrast varies, sometimes, below 550 nm or above 500 nm, depending on the relation between the TiN reflectivity and the background (underlayer) reflectivity. Thus, considering a spectral optical constant of the material used for the semiconductor, it is effective in performing a highly sensitive inspection on a wide range of wafers of various structures and processes to make it possible to illuminate on both sides—shorter side and longer side—of the wavelength range in which optical constants (n, k) change.

As described above, a wavelength band that mostly satisfies the wavelength conditions for minimizing the thin film interferences and for detecting defects with high contrast is around 365-700 nm. As the illumination wavelength on the shorter side, a wavelength of 193-313 nm (e.g., 198 nm, 248 nm, 266 nm and 313 nm), shorter than 365 nm, may be prepared. With this arrangement an optical system is realized that can cope with new materials and new structures of future semiconductors and also deal with requirements for further miniaturization.

Since materials used in the optical system that realizes an aberration correction in a range from DUV to visible light are limited, the design and manufacture are difficult. Particularly, the objective lens is highly difficult to manufacture and it is also difficult to satisfy three requirements—wide-band wavelength, high NA (Numerical Aperture) and wide field of view.

Thus, in this variation, an example method and apparatus will be explained in which an illumination light emitted from a light source of wide-band wavelength is divided into smaller bands of wavelength and in which images are taken for each of the divided wavelength bands for defect extraction.

FIG. 4 shows a construction of an illumination optical system and a detection optical system that together generate, through image processing, a combined image during the wide-band wavelength illumination by using objective lenses 72, 73 assigned with two divided aberration correction wavelength bands. The illumination system has almost the same construction as shown in FIG. 2 and identical components are given like reference numbers. An illumination beam of wide wavelength band that was emitted from the light source 20 and has passed through the beam splitter 65, now enters a dichroic mirror 180, which passes a visible beam (450-650 nm) and reflects light in a range between ultraviolet and visible light (360-440 nm). The light that has passed through the dichroic mirror 180 enters a visible light objective 73, whose aberration was corrected in the visible wavelength range, illuminating the wafer 1. The reflected light or detection light passes through the dichroic mirror 180 again and enters the beam splitter 65. The light that is reflected by the beam splitter 65 and passes through a dichroic mirror 181 is introduced into a visible light detection system, in which the light passes through a beam splitter 85a and through a lens 95a, an analyzer 80a and a lens 121a and is led into a spatial filter 130a situated at a position conjugate with the pupil of the objective 73. The light that has passed through the spatial filter 130a focuses an image of the surface of the wafer 1 through a lens 122a onto an image sensor 100a. The light that was reflected by the beam splitter 85a becomes a focus detection beam which enters into a focus detection system of the same construction as explained in FIG. 2, forming an image of the stripe pattern 59 through an image forming lens 88. The focus detection system then detects a difference between the wafer 1 and the focal position and drives the Z stage 212 for focus alignment.

The UV-visible beam reflected by the dichroic mirror 180 of the illumination system is introduced by a mirror 175 into a UV-visible light objective 72, that is aberration-corrected in the UV-visible wavelength range, to illuminate the wafer 1. The light that is reflected by the wafer 1 is again captured by the UV-visible light objective 72 and again reflected as a detection light by the dichroic mirror 180 to enter the beam splitter 65. The detection light with a wavelength of 360-440 nm that was reflected by the beam splitter 65 is further reflected by the dichroic mirror 181 and introduced into the detection system that detects light in the UV-visible wavelength range. The light then enters a beam splitter 85b. A part of the detection light that has entered the beam splitter 85b passes through it, travels through a lens 95b, an analyzer 80b and a lens 121b and reaches a spatial filter 131b situated at a position conjugate with the pupil of the objective 72. The light that has passed through this spatial filter 131b without being interrupted forms an image of the surface of the wafer 1 on an image sensor 100b through a lens 122b. The light that was reflected by the beam splitter 85b becomes a focus detection beam for the UV-visible light objective 72. The focus detection beam then enters a focus detection system 93b of the same construction as explained in FIG. 2, which detects a difference between the wafer 1 and the focal position of the UV-visible light objective 72 and vertically drives the objective 72 to match its focus with the wafer 1.

The images detected by the visible light image sensor 100a and the UV-visible light image sensor 100b at the same time are images at different positions on the wafer 1 and thus must be combined to generate a synthesized image at the same position on the wafer 1. Therefore, assuming that the wafer 1 is moving at a constant speed from left to right as shown by an arrow 3, the analog image signal detected by the UV-visible light image sensor 100b is A/D-converted by an A/D converter 110b and then stored temporarily in a delay memory 400. The time for which the digital image signal is temporarily stored in the delay memory 400 corresponds to the time it takes for the visible light image sensor 100a to detect an image at the same position as the image detected by the UV-visible light image sensor 100b. This time is determined by the stage moving speed and the distance between the UV-visible light objective 72 and the visible light objective 73.

The analog signal detected by the visible light image sensor 100a is A/D-converted by an A/D converter 110a before being fed to an image synthesizing unit 410. In the image synthesizing unit 410, the digital image is then combined with the digital image that was obtained by detecting optical images in the UV-visible wavelength range successively fed from the lens distance-sensitive delay memory 400, thereby forming an averaged synthesized image. By using this synthesized image, the image processing unit 300 makes decision on defects, thereby generating a UV-visible light (360-650 nm) image. It is therefore possible to generate an image that minimizes sensitivity impairing factors and enhances the contrast of defects allowing for highly precise decisions on defects. The synthesized image may be made, rather than by adopting the average of the UV-visible light image and the visible light image, but by changing a weight ratio between the UV and UV-visible light images (e.g., UV 1:UV-visible 2) in a way that assures a highly sensitive detection, according to the contrasts of pseudo defects and defects. In this construction, the dichroic mirror 180 installed in the illumination system and the dichroic mirror 181 installed in the detection system have the same characteristics. The use of the dichroic mirrors of the same characteristics offers an advantage of reducing parts cost. Although this embodiment has explained about an example of UV-visible wavelength range, it is easily conceived to change the wavelength range to a DUV-visible range. It is obvious that the latter wavelength range also falls within a scope of this invention.

Figure 5:
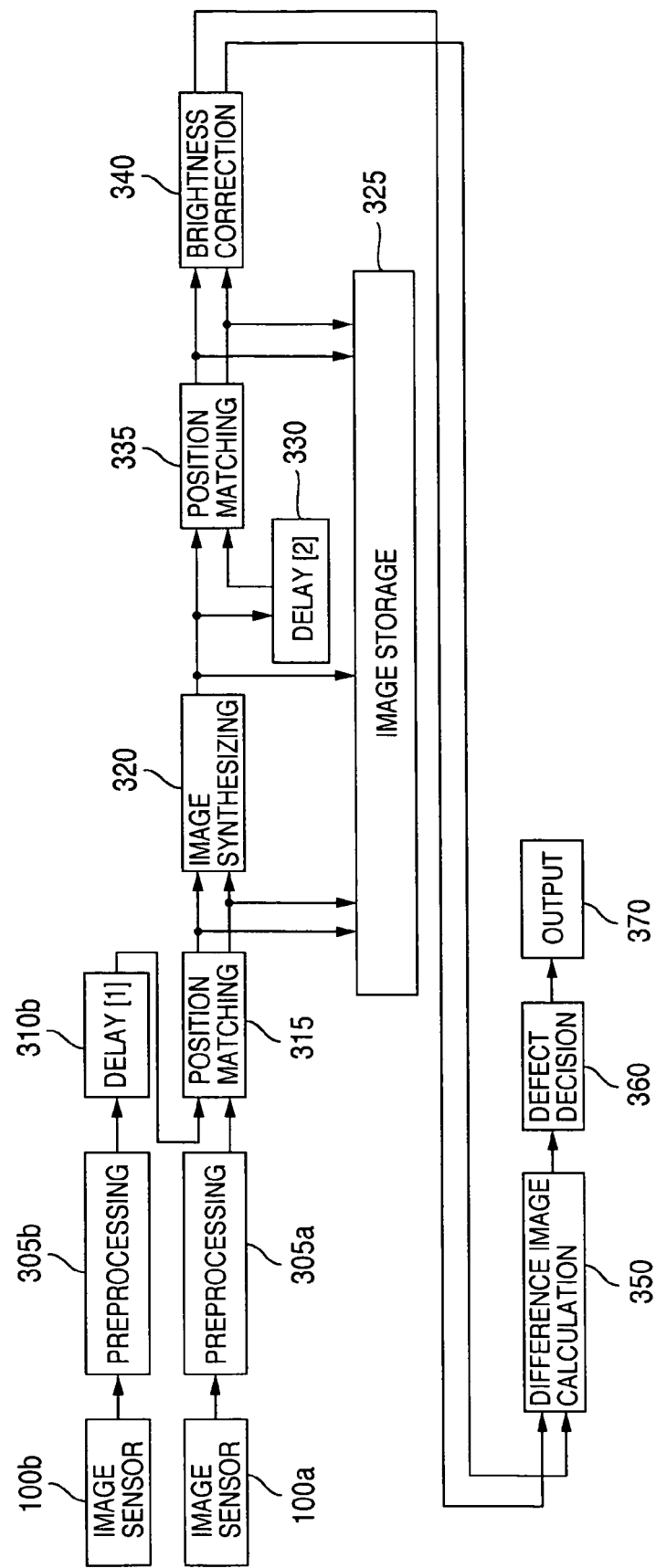
FIG. 5 is a block diagram showing a flow of signal processing to explain about an image processing function.

FIG. 5 shows a defect decision process that uses the images of 2-illumination wavelength band of the variation 2 explained with reference to FIG. 4. The UV-visible light image detected by the UV-visible light image sensor 100b is A/D-converted and then subjected to preprocessing 305b that corrects ununiformity of images according to a luminance distribution in the field of view and a uniformity of sensor's sensitivity. This preprocessing 305b also includes nonlinear image brightness conversion such as correction of images. The preprocessed image is temporarily stored in a delay memory [1]. The visible light image detected by the visible light image sensor 100a is similarly preprocessed at 305a before being fed to a position matching unit 315. The UV-visible light image corresponding to the same position of this image is also fed from the delay memory [1] to the position matching unit 315. In order to combine these images so that the same wafer positions aligningly overlap, the image positions are aligned for each pixel or for each subpixel.

Figure 11:
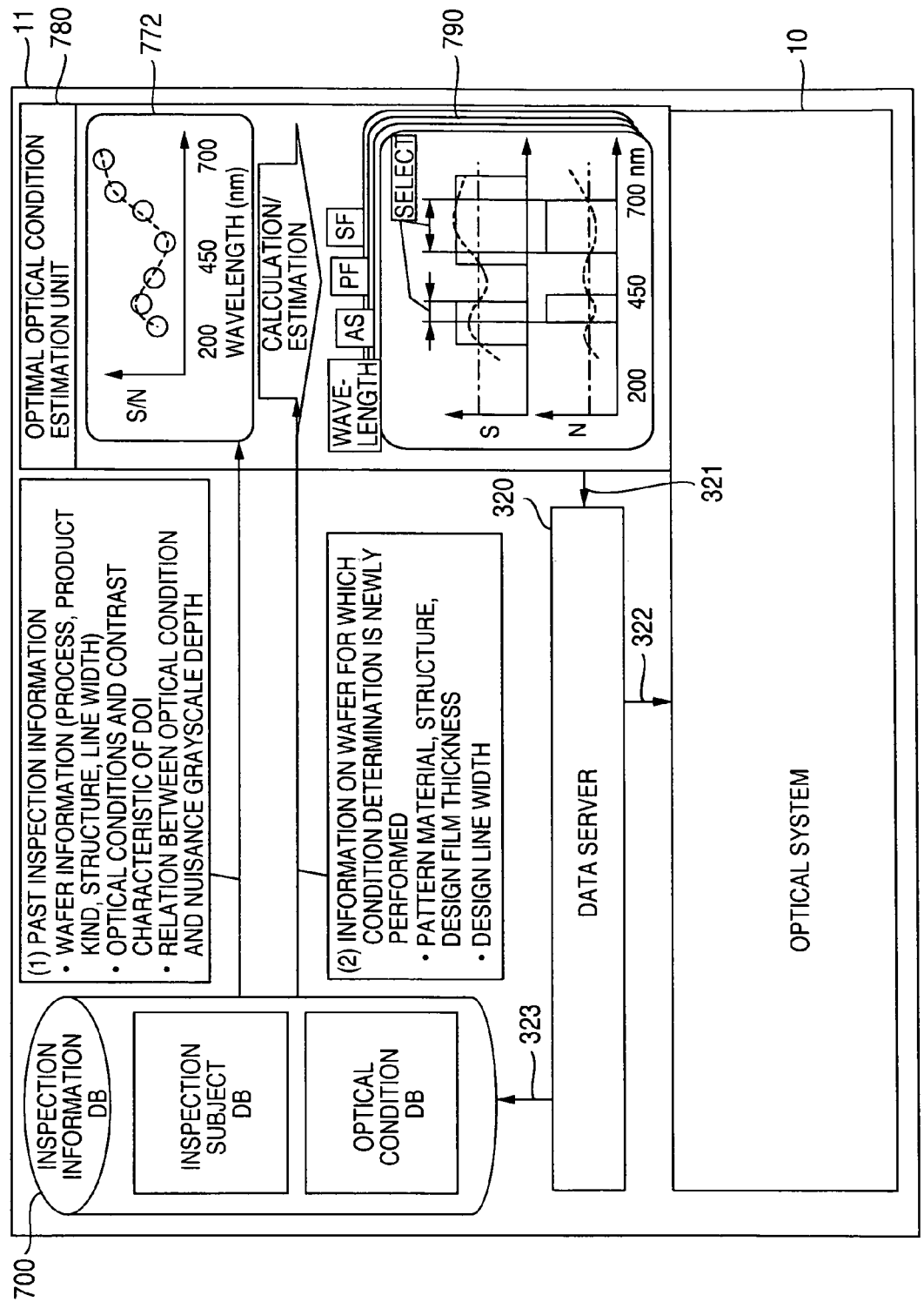
FIG. 11 is a block diagram showing an overall configuration of the inspection apparatus including the inspection information database.

The images that were aligned in position are stored in an image storage unit 325 and at the same time sent to an image synthesizing unit 320 which generates an averaged image of two images or a synthesized image so weighted as to improve the defect decision accuracy. The weighting advantageous to the defect decision will be explained by referring to FIG. 11 and FIG. 12. The synthesized image also is temporarily stored in the image storage unit 325 and at the same time fed to a delay memory [2] 330 and a position matching unit 335. The synthesized image corresponding to an adjoining die or adjoining cell is fed from the delay memory [2] 330 to the position matching unit 335, where it is position-aligned with that image directly sent to the position matching unit 335 which is the same pattern in design but located at a spatially different position. After this, a brightness correction unit 340 corrects a brightness difference between the two images which is a hindrance to the comparison and decision and a difference image is calculated by a difference image calculation unit 350. A defect decision unit 360 uses characteristic quantities of this difference image (e.g., magnitudes of grayscale depths, brightness of images before the difference image is calculated, brightness of images before and after brightness correction is made, distributions of these brightnesses, and distributions of grayscale depths of portions surrounding defects) to make a decision on defect candidates.

The characteristic quantities and coordinates obtained from the result of decisions are stored in a data server 330 of FIG. 1 as inspection result information. Further, of the images stored in the image storage unit 325, images near the defect candidates and images of the portions used for comparison are picked up and stored as the inspection result information in the data server 330 of FIG. 1. Further, as for the images of other than the defect candidates, they are eliminated so that the memory capacity of the image storage unit 325 will not be saturated.

Using the images of portions close to the defect candidates and the images of portions used for comparison, an automatic defect classification is performed. In performing this classification, it is possible to use two kinds of defect images with different illumination wavelength bands and two kinds of normal portion images with different illumination wavelength bands. Thus, by comparing the brightnesses of the two kinds of defect images (two illumination bands), a defect classification can be made based on spectral reflectivity characteristics, thus contributing to improvements in a classification performance. This information is also stored in the inspection result information. Further, as for the results of the automatic defect classification and the images of defects classified into the same category and of those portions used for comparison with these defects, only representative images in each category are stored. Other images may be deleted or stored in other data servers to which data can be transferred from the inspection apparatus, in order to alleviate the storage capacity required of the inspection apparatus.

For the steps following the optical condition determination step, the same procedure that was explained in the embodiment 1 applies.

[Variation 3]

A third variation of the defect decision method using the images detected by the two image sensors of FIG. 4 will be explained by referring to FIG. 6. This method performs defect decisions on the UV-visible light image detected by the image sensor 100*b* and on the visible light image detected by the image sensor 100*a* by using the respective image processing systems to output defect candidates.

First, a flow of a UV-visible light image detected by the image sensor 100*b* will be explained. After being A/D-converted, an image signal is subjected to preprocessing 305*b* to correct unevenness of the image according to illumination distribution in the field of view and the uniformity of sensor sensitivity. The preprocessed image is sent to a delay memory 330*b* and a position matching unit 335*b*. The image corresponding to an adjoining die or adjoining cell is fed from the delay memory 330*b* to the position matching unit 335*b*, where it is position-aligned with that image directly sent to the position matching unit 335*b* which is the same pattern in design but located at a spatially different position. After this, a brightness correction unit 340*b* corrects a brightness difference so that the two images of normal patterns have equal brightness, and a difference image is calculated by a difference image calculation unit 350*b*. A defect decision unit 360*b* outputs characteristic quantities of this difference image and coordinates, which are stored as the inspection result information. Of the images stored in the image storage unit 325*b*, images near the defect candidates and images of the portions used for comparison are picked up and stored as the inspection result information.

The same processing as described above is executed for the visible light image detected by the image sensor 100*a* (from 305*a* to 360*a*) and the inspection result information is output (370).

The defects detected by these two systems are checked by using their coordinates. If the same defects are detected, they are handled as one defect so that they are not counted as different defects in the reported result. One advantage of this method is as follows. That is, if a UV-visible light image produced is darker than the normal portion to be compared and a visible light image produced is brighter than the normal portion to be compared, the average image shown in FIG. 5 may have a smaller grayscale depth for the defect portions, making it impossible to determine them to be defects. In contrast, the configuration shown in FIG. 6 can solve this problem. Although FIGS. 4 to 6 show an example configuration in which the illumination wavelength band is divided into two systems, it is theoretically desirable to increase the number of bands into which the wavelength band is divided. For example, it is advantageous if the wavelength range is divided into five bands, e.g., DUV, UV, visible blue, visible green and visible red. In that case, most of the wavelength range on the shorter and longer wavelength side of a point of change of a spectral constant and spectral reflectivity of the material used in the semiconductor can be covered. However, an increased size of the optical system unavoidably increases the cost. Therefore, to cover a wide range of inspection process for semiconductor requires an optical system capable of illuminating at least in a UV to visible wavelength range.

Embodiment 2

Figure 7:
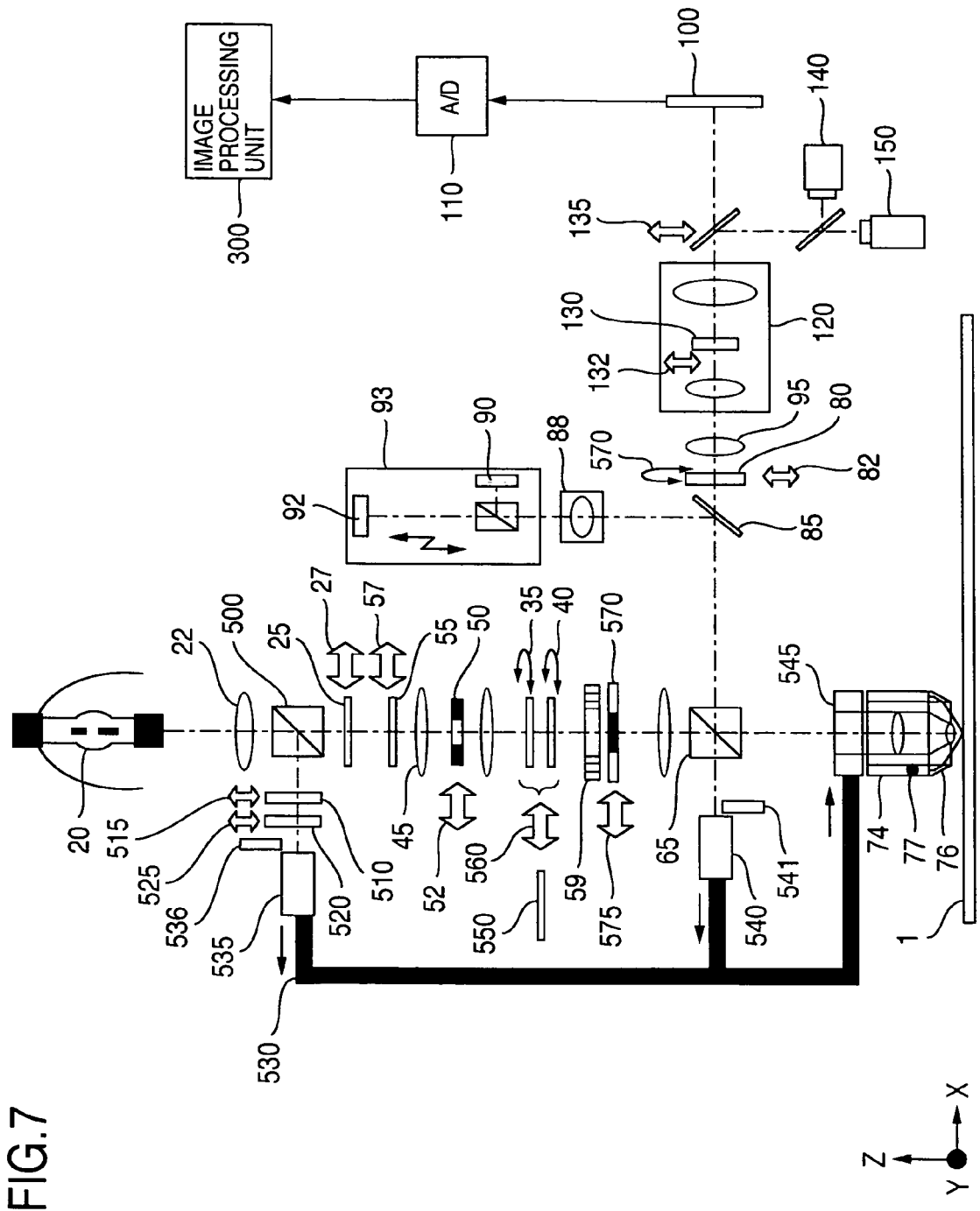
FIG. 7 is a front view showing an outline construction of an optical system of an optical appearance inspection device as a second embodiment of the invention.

A detection system of microscope is largely classified into a bright-field detection and a dark-field detection. Depending on the detection principle, some defects are easily detected and some are not. For example, the bright-field detection system can easily detect small-step thin film residues, fine shorted defects and pattern shape anomalies. The dark-field detection system can advantageously detect stepped defects, such as foreign matters and scratches. In metal wiring patterns (e.g., aluminum wiring), grains may occur on the pattern of a surface. The grains have little adverse effects on the electrical characteristics of devices and thus should preferably not be detected as defects. For this reason, they are called pseudo defects and a defect decision threshold in the inspection apparatus needs to be adjusted in a way that does not detect the grains. As for the grains, a composite illumination of the bright- and dark-field illuminations may be used to reduce the contrast of the grains, which offers an advantage of being able to improve the inspection sensitivity thanks to a reduction in the defect decision threshold. FIG. 7 shows a construction of a multipurpose optical system that realizes a bright-/dark-field composite illumination, a UV-visible wavelength wide band illumination, a polarized illumination/detection, and an irregular illumination/spatial filtering.

Light from a Hg—Xe lamp that emits light of a wide wavelength band, for example, passes through a lens 22 into a PBS (Polarizing Beam Splitter) 500, by which an S-polarized component is reflected to enter a dark-field illumination lightguide 530. In front of a lightguide incident end 535 are arranged a light quantity adjustment ND filter 510 and an interference filter 520 to select a dark-field illumination wavelength range. The ND filter 510 comprises a plurality of filters with different transmissivities and the interference filter 520 comprises a plurality of filters with different spectral transmittances. There are mechanisms 515, 525 one for each kind of filter to select one of the filters. This lightguide incident portion is divided into two branches. The other incident end 540 is arranged to receive light that is reflected by the beam splitter 65 with little polarization dependency. An outgoing end 545 of the lightguide 530 is arranged near a framed objective 74, and optical fibers making up the lightguide 530 are arranged in a ring configuration around a light axis of the objective 74. Beams emitted from these optical fibers pass through a hollow portion 77 on the outside of the objective 74 and are reflected by a concave mirror 76 to illuminate the wafer 1. An inner surface of the hollow portion 77 is given a mirror surface treatment to enhance a light reflectivity. Although this figure shows the ring-shaped optical fibers to be disposed above the framed objective 74, it is possible to arrange a ring-shaped concave mirror below the objective 74 (immediately above the wafer) to collect beams into the field of view of the objective 74 above the wafer 1.

The P-polarized beam that has passed through the PBS 500 travels through the wavelength selection filter 25. The wavelength selection filter 25 has a plurality of filters with different spectral transmittances and a mechanism 27 is provided which can select a desired filter. If there is no need to select (limit) the illumination wavelength, the wavelength selection filter may not be installed in the illumination path and an illumination may be performed in a wide wavelength range. Next, the light is adjusted in its light quantity by the ND filter 55 with a selection mechanism 57 and, through a lens 45, forms an image of the light source at a position of the diaphragm 50 with a selection mechanism 52. The light that has passed through the diaphragm 50 illuminates the AF stripe pattern 59 situated at a position conjugate with the wafer 1 and the light that has passed through the beam splitter 65 projects the image of the stripe pattern 59 onto the wafer 1 through the objective 74.

The detection light quantity ratio between the bright-field illumination light and the dark-field illumination light can be adjusted by a dark-field ND filter 510 and a bright-field ND filter 55. The light quantity ratio is determined by checking the inspection sensitivity when preparing an inspection recipe. When it is desired to detect only a bright-field image, rather than using a bright-/dark-field composite illumination, shutters 536, 541 installed in front of the two-pronged incident ends 535, 540 of the dark-field lightguide are closed. When it is desired to detect only a dark-field image, a viewing field limiting mask 570 arranged near the viewing field diaphragm position (AF stripe pattern 59) is inserted. This inserts a mask corresponding to a range of image detection by the image sensor 100. Since the outside of the image detection range is illuminated, the AF stripe pattern 59 is also projected, allowing the AF detection system 93 to detect a deviation between the focus of the objective 74 and the wafer 1. This in turn enables the automatic focus control to be performed.

Of the beams that were reflected, diffracted and scattered on the wafer 1, the beam captured by the objective 74 is reflected by the beam splitter 65 and introduced into a detection path where it is then branched by the beam splitter 85 into an AF light path and an image detection light path. In the AF light path, the image forming lens 88 forms an image of the stripe pattern reflected from the wafer 1. AF image sensors 90, 92 are located a predetermined distance from this image plane on the wafer side and on the opposite side. The focus state of the wafer is detected based on the contrasts of the stripe pattern images detected by the two sensors 90, 92. The beam that passed through the beam splitter and was introduced into the image detection light path now enters the analyzer 80 that allows only an electric field vector that oscillates in a predetermined direction to pass therethrough.

The light transmission axis of the analyzer 80 is adjustable by a mechanism 570 because the direction conducive to enhancing the contrast changes according to the material and structure/dimension of the defects and the positional relation with a nearby pattern. The light that has passed through the analyzer 80 forms an optical image of the wafer 1 once through the image forming lens 95. This image is projected onto the image sensor 100 through a zoom lens 120. The zoom lens 120 is provided with a position conjugate with a pupil of the objective 70. At this position a spatial filter 130 can be installed. The spatial filter 130 comprises a plurality of filters with different shapes, transmissivities and phases. There is also a mechanism 132 that can set a desired spatial filter 130 conducive to an enhanced contrast of the defects. This optical system is mounted with a defect review camera 140 and a wafer alignment camera 150.

Since, with a linearly polarized illumination, defect emphasis has a directional dependency and material and structural dependencies, the linearly polarized beam may be rotated to set a condition that allows a target defect to be detected with high contrast. For this purpose, a rotatable half waveplate 35 and a rotatable quarter waveplate 40, which is used for elliptically polarized illumination, are installed in the illumination path on the wafer 1 side of the PBS 500. If a sufficient defect contrast can be obtained with only the polarized illumination, the analyzer 80 may be removed from the light path to improve the efficiency of the detection light quantity. For this purpose, the analyzer 80 may be mounted on a mechanism that removes it from the light path. Further, if more varied ranges of defects can be detected by not using the polarized illumination, a depolarizer 550 may be installed in the illumination light path on the wafer 1 side, rather than on the PBS 500 side, to cancel the polarization. For example, when one wishes to use a randomly polarized illumination, a mechanism 560 may be provided that puts the depolarizer 550 in the illumination path, instead of retracting the half waveplate 35 and quarter waveplate 40. This makes it possible to select a desired polarized or non-polarized illumination, thus realizing an illumination conducive to the detection of various kinds of defects.

In this embodiment, the step of processing the image detected by the image sensor 100 and the subsequent steps are similar to those explained in embodiment 1. The optical condition determination, such as the selection of illumination system (bright-field illumination, dark-field illumination and bright-/dark-field composite illumination) and of illumination wavelength, is as shown in FIGS. 8 to 13.

As for the construction, function and condition determination described in the above embodiments, a variety of combinations may be possible and it is apparent that these combinations are also within the scope of this invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description. All changes which come within the meaning and range of equivalency of the claims are therefore intended to be embraced therein.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A defect inspection apparatus comprising:
light source means for emitting light having a wavelength band in a range from an ultra-violet light range to a visible light range;
light illuminating means including a wavelength selection unit for selecting a light beam having a desired wavelength from the light of the wavelength band emitted by the light source means and illuminating a specimen on which a wire pattern is formed with the selected light beam;
detection means for receiving an optical image of the specimen illuminated with the light beam having the desired wavelength from the light illuminating means and outputting an image signal of the received optical image of the specimen;
image processing means for processing the image signal output from the detection means to detect defects;
control means for controlling at least one of the light source means, the light illuminating means, the image detection means and the image processing means;
inspection information display means displaying on a screen data corresponding to the specimen and data corresponding to optical conditions of at least one of the light source means, the light illumination means, the image detection means and the image processing means; and
input means for inputting information corresponding to a defect of interest and corresponding to the specimen including kind of specimen, process and lot number;
wherein the control means, based on the information input from the input means, controls the wavelength selection unit to select the desired wavelength of the light beam to illuminate the specimen.

2. A defect inspection apparatus according to claim 1, wherein the light illuminating means further includes an illumination polarization control unit to control a polarized state of the selected beam of the desired wavelength.

3. A defect inspection apparatus according to claim 1, wherein the detection means controls the polarized state of the optical image of the specimen to be received.

4. A defect inspection apparatus comprising:
light source means for emitting light having a wavelength band in a range from an ultra-violet light range to a visible light range;
light illuminating means for selecting a light beam having a desired wavelength from the wavelength band emitted by the light source means, adjusting a polarized state of the selected light beam of the desired wavelength, and radiating the polarization state adjusted light beam onto a specimen on which a wire pattern is formed;
detection means for receiving an optical image of the specimen illuminated with the light beam of the desired wavelength from the light illuminating means and outputting an image signal of the received optical image of the specimen;
image processing means for processing the image signal output from the detection means to detect defects;
input means for inputting information corresponding to a defect of interest and corresponding to the specimen including kind of specimen, process and lot number; and
control means for controlling in accordance with the inputted information from the input means at least the selection of the light beam of the desired wavelength performed by the light illuminating means and for controlling the adjustment of the polarized state performed by the light illuminating means.

5. A defect inspection apparatus according to claim 4, wherein the control means controls the adjustment of the polarized state performed by the light illuminating means in accordance with the inputted information from the input means.

6. A defect inspection method comprising the steps of:
selecting a light beam having a desired wavelength from a light having a wavelength band in a range from an ultra-violet light range to a visible light range emitted from a light source and illuminating a specimen on which a wire pattern is formed with the selected light beam;
photographing an optical image of the specimen illuminated by the light beam of the desired wavelength to obtain an image signal;
processing the obtained image signal to detect defects;
wherein the step of selecting the light beam of the desired wavelength is effected by using information which is input including information corresponding to a defect of interest and corresponding to the specimen including kind of specimen, process and lot number.

7. A defect inspection method comprising the steps of:
selecting a light beam having a desired wavelength from a light having a wavelength band in a range from an ultra-violet light range to a visible light range emitted from a light source;
controlling a polarized state of the selected light beam of the desired wavelength and illuminating the selected light beam onto a specimen on which a wire pattern is formed;
photographing an optical image of the specimen illuminated with the light beam of the desired wavelength by controlling the polarized state of the light beam; and
processing the photographed image;
wherein the step of selecting the light beam having the desired wavelength, the step of controlling the polarized state of the selected light beam, the step of photographing the optical image of the specimen, and the step of processing the photographed image are effected by referencing past data accumulated in a database by using information on a material of the wire pattern formed on the specimen.

* * * * *